(12) United States Patent
Carpenter et al.

(10) Patent No.: US 7,794,706 B2
(45) Date of Patent: Sep. 14, 2010

(54) BIOACTIVE WOUND DRESSINGS AND IMPLANTABLE DEVICES AND METHODS OF USE

(75) Inventors: Kenneth W. Carpenter, La Jolla, CA (US); William G. Turnell, San Diego, CA (US); Kristin M. DeFife, San Diego, CA (US); Kathryn A. Grako, San Diego, CA (US); Ramaz Katsarava, Tbillsi, GA (US)

(73) Assignee: Medivas, LLC, San Diego, CA (US)

( * ) Notice: Subject to any disclaimer, the term of this patent is extended or adjusted under 35 U.S.C. 154(b) by 0 days.

(21) Appl. No.: 11/796,267

(22) Filed: Apr. 26, 2007

(65) Prior Publication Data

US 2008/0020015 A1   Jan. 24, 2008

Related U.S. Application Data

(63) Continuation-in-part of application No. PCT/US2005/038925, filed on Oct. 27, 2005, and a continuation-in-part of application No. 10/362,848, filed on Oct. 14, 2003.

(60) Provisional application No. 60/623,446, filed on Oct. 28, 2004.

(51) Int. Cl.
  *C12N 11/08*   (2006.01)

(52) U.S. Cl. ............ 424/93.7; 424/497; 424/443; 528/176; 528/179; 528/182; 528/184; 528/189; 528/332; 528/335; 528/336; 528/339; 524/86; 524/333

(58) Field of Classification Search ............. None
See application file for complete search history.

(56) References Cited

U.S. PATENT DOCUMENTS

| 5,906,934 A | * | 5/1999 | Grande et al. | ............ 435/325 |
| 6,171,610 B1 | | 1/2001 | Vacanti et al. | ............ 424/426 |
| 7,396,537 B1 | * | 7/2008 | Krupnick et al. | ............ 424/400 |

FOREIGN PATENT DOCUMENTS

| WO | WO 02/18477 A2 | 3/2002 |
| WO | WO 02/18477 A3 | 3/2002 |

OTHER PUBLICATIONS

Chunmeng et al., "Effects of Dermal Multipotent Cell Transplantation on Skin Wound Healing", *Journal of Surgical Research*, 121:13-19 (2004).

Yamaguchi et al., "Bone marrow cells differentiate into wound myofibroblasts and accelerate the healing of wounds with exposed bones when combined with an occlusive dressing", *British Journal of Dermatology*, 152:616-622 (2005).

* cited by examiner

*Primary Examiner*—Allison M Ford
(74) *Attorney, Agent, or Firm*—DLA Piper LLP (US)

(57) ABSTRACT

The present invention provides wound dressings, optionally surgically implantable, containing biodegradable, polymers and hydrogels having allogenic or autologous precursor cells, such as stem cells and progenitor cells dispersed within. Alternatively, the wound dressings can have conditioned medium obtained from the precursor cells dispersed within. The wound dressings promote tissue restoration processes at a site of application or implantation. Additional bioactive agents can also be dispersed within the polymer/hydrogel matrix, which can be formulated to biodegrade at a controlled rate by adjusting the composition. Methods are also provided for using such biodegradable wound dressings as a delivery device or carrier for the precursor cells, conditioned medium and bioactive agents, or as coatings on implantable medical devices, to promote tissue restoration at a lesion site.

32 Claims, 1 Drawing Sheet

BIOACTIVE WOUND DRESSINGS AND IMPLANTABLE DEVICES AND METHODS OF USE

CROSS REFERENCE TO RELATED APPLICATIONS

Figure 1:
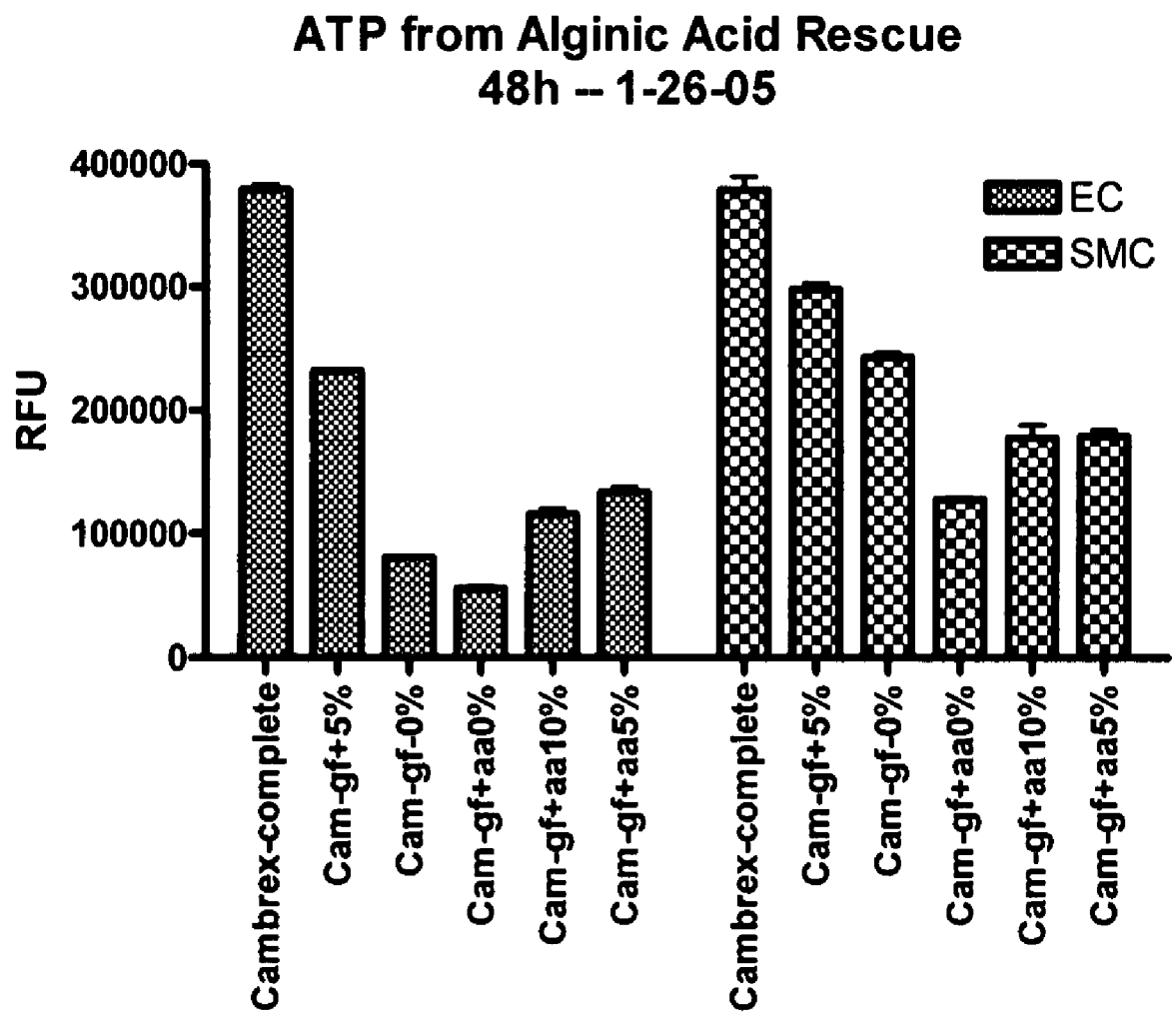

This application claims the priority benefit under 35 USC §365(c) as a continuation-in-part application of International Patent Application No. PCT/US2005/038925, filed Oct. 27, 2005, which claims the priority benefit under 35 USC §119(e) to U.S. provisional application No. 60/623,446, filed Oct. 28, 2004; and this application is a continuation-in-part of U.S. application Ser. No. 10/362,848, filed Oct. 14, 2003, now U.S. Pat. No. 7,304,122, which is the national stage entry of PCT/US2001/027288, filed Aug. 30, 2001, which is a continuation of U.S. application Ser. No. 09/651,338, filed Aug. 30, 2000, now U.S. Pat. No. 6,503,538. The disclosure of the prior applications is considered part of and is incorporated by reference in the disclosure of this application.

FIELD OF THE INVENTION

The invention relates generally to compositions used in healing wounds and lesions, and in particular to biodegradable polymer dressings that promote natural healing processes at wound sites.

BACKGROUND INFORMATION

In general, wounds and lesions can be divided into two types: acute and chronic. In cases where a wound is not initially surgically closed (delayed primary closure), the wound is left open for a time sufficient to allow the inflammatory process and angiogenesis to begin before surgical closure. Wounds healing by secondary intention are usually not amenable to surgical closure. As a result, the wound is left to granulate and epithelialize from the wound bed and edges. Numerous dressing products were developed during the past few years to accelerate this type of healing process.

For these types of acute wounds, occlusive dressings increase re-epithelialization rates by 30% to 50% and collagen synthesis by 20% to 60% compared to wounds exposed to air by providing an optimal healing environment that exposes the wound continuously to the surrounding fluid of proteinases, chemotactic factors, complements, and growth factors. An electrical gradient that may stimulate fibroblast and epithelial cell migration is maintained. The use of nonadherent dressing prevents the stripping of the newly formed epithelial layer.

An occlusive dressing is generally divided into a hydrating layer (antibiotic ointments or petrolatum jelly), a nonadherent contact layer, an absorbent and cushioning layer (gauze), and a securing layer (tape or wrap). Occlusive dressings are commonly applied within 2 hours of wounding and left on for at least 24 hours, rarely as long as 48 hours, for optimal healing of acute wounds. Initial wound hypoxia is important for fibroblast proliferation and angiogenesis; however, continued hypoxia at the wound site delays wound healing. As a result, if an occlusive dressing is applied to an ischemic wound, healing is severely impaired.

Chronic wounds are defined as wounds that fail to heal after 3 months. Venous stasis ulcers, diabetic ulcers, pressure ulcers, and ischemic ulcers are the most common chronic wounds. Many of the dressing options that attempt to heal venous stasis ulcers are a variation on the classic paste compression bandage, Unna's boot. These wounds can sometimes have large amounts of exudates that require frequent debridement. Alginates, foams, and other absorptives can be used in this situation. Because chronic wounds heal by slightly different mechanisms than those of acute wounds, experimentation with growth factors is being investigated. Regranex® and Procuren® (Curative Health Services, Inc., Hauppauge, N.Y.) are the only medications approved by the US Food and Drug Administration (FDA).

Despite these advances in the art, a need exists in the art for new and better methods and devices for restoring the natural process of wound healing at a lesion, the repair of which requires tissue remodeling and restoration.

SUMMARY OF THE INVENTION

The present invention is based on the premise that multiple complex processes, involving the differential expression of dozens if not hundreds of genes, are necessary for optimal tissue repair and remodeling. Based on this concept, it follows that optimal repair of wounds and lesions cannot be achieved by the administration of single proteins, or single genes whose encoded products are known to be related to such processes nor, because of the complexity of tissue restoration processes, by the administration of a combination of related proteins or genes. This invention relies on the capacity of certain precursor cells, such as tissue-specific progenitor cells, to secrete the various factors, such as growth factors and cytokines, involved in tissue restoration in a time and concentration-dependent coordinated and appropriate sequence.

The present invention is based on the discovery that a biodegradable polymer or hydrogel can be loaded with allogenic or autologous precursor cells, conditioned medium obtained from such precursor cells, or a combination thereof, and used to recruit and/or to hold autologous natural healing cells at a lesion, the repair of which requires tissue remodeling and restoration. Tissue restoration is the process whereby multiple damaged cell types are replaced to restore the histoarchitecture and function to the treated tissue. The precursor cells are protected, nurtured in growth medium, and delivered by the biodegradable polymer(s) and/or hydrogels in the invention wound dressings and device coatings.

Accordingly, in one embodiment, the invention provides bioactive wound dressings in which at least one precursor cell selected from stem cells, tissue-specific progenitor cells, germ-layer lineage stem cells, and pluripotent stem cells, conditioned medium obtained from such cells, and combinations thereof is dispersed within a biodegradable polymer or hydrogel.

In another embodiment, the invention provides methods for promoting restoration of tissue at a lesion site in a mammalian subject by contacting the lesion site with an invention wound dressing under conditions suitable for promoting restoration of the tissue at the lesion site, wherein the wound dressing comprises at least one precursor cell selected from stem cells, tissue-specific progenitor cells, germ-layer lineage stem cells, pluripotent stem cells, conditioned medium obtained from such cells, and combinations thereof, dispersed within a biodegradable polymer or hydrogel.

In still anther embodiment, the invention provides polymer coatings for coating at least a portion of an implantable medical device. The invention polymer coatings include a biodegradable polymer having dispersed therein at least one precursor cell selected from stem cells, tissue-specific progenitor cells, germ-layer lineage stem cells, and pluripotent stem cells, conditioned medium obtained from such cells, and combinations thereof, to enhance tissue restoration at the site of implantation. The biodegradable polymer used is a PEA having a chemical structure described by structural formula (I),

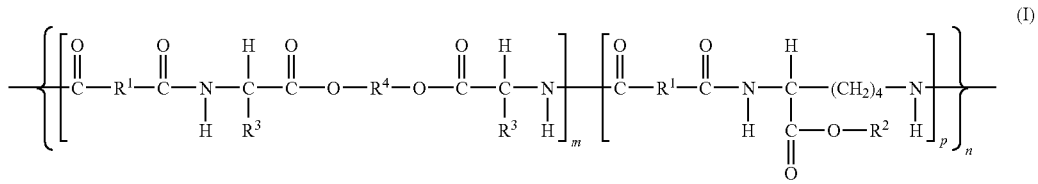

and wherein n ranges from about 5 to about 150, m ranges about 0.1 to about 0.9: p ranges from about 0.9 to about 0.1; wherein $R^1$ is selected from the group consisting of $(C_2\text{-}C_{20})$ alkylene or $(C_2\text{-}C_{20})$alkenylene; $R^2$ is hydrogen or $(C_6\text{-}C_{10})$aryl$(C_1\text{-}C_6)$alkyl or t-butyl or other protecting group; $R^3$ is selected from the group consisting of hydrogen, $(C_1\text{-}C_6)$ alkyl, $(C_2\text{-}C_6)$alkenyl, $(C_2\text{-}C_6)$alkynyl and $(C_6\text{-}C_{10})$aryl$(C_1\text{-}C_6)$alkyl; and $R^4$ is selected from the group consisting of $(C_2\text{-}C_{20})$alkylene, $(C_2\text{-}C_{20})$alkenylene or $(C_2\text{-}C_{20})$alkyloxy $(C_2\text{-}C_{20})$alkylene, and bicyclic-fragments of 1,4:3,6-dianhydrohexitols of general formula (II):

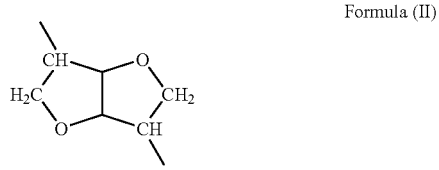

Formula (II)

except that for unsaturated polymers having the chemical structure of structural formula (I), $R^1$ and $R^4$ are selected from $(C_2\text{-}C_{20})$alkylene and $(C_2\text{-}C_{20})$alkenylene; wherein at least one of $R^1$ and $R^4$ is $(C_2\text{-}C_{20})$alkenylene; n is about 5 to about 150; each $R^2$ is independently hydrogen, or $(C_6\text{-}C_{10})$aryl$(C_1\text{-}C_6)$alkyl; and each $R^3$ is independently hydrogen, $(C_1\text{-}C_6)$ alkyl, $(C_2\text{-}C_6)$alkenyl, $(C_2\text{-}C_6)$alkynyl, or $(C_6\text{-}C_{10})$aryl$(C_1\text{-}C_6)$alkyl, or a PEUR having a chemical formula described by structural formula (III), (II); and $R^6$ is independently selected from $(C_2\text{-}C_{20})$alkylene, $(C_2\text{-}C_{20})$alkenylene or alkyloxy, and bicyclic-fragments of 1,4:3,6-dianhydrohexitols of general formula (II), except that for unsaturated polymers having the structural formula (III) $R^6$ and $R^4$ are selected from $(C_2\text{-}C_{20})$alkylene and $(C_2\text{-}C_{20})$alkenylene; wherein at least one of $R^6$ and $R^4$ is $(C_2\text{-}C_{20})$alkenylene, wherein the wound dressing promotes in vivo tissue repair or remodeling at a site at which the device is implanted in a subject.

A BRIEF DESCRIPTION OF THE FIGURE

FIG. 1 is a graph showing the ATP generated in 48 hours by smooth muscle cells plated in Cambrex-complete-media (growth factors plus 5% fetal bovine serum (FBS)), Cambrex-minus-growth-factors (gf)-plus-5% FBS, or Cambrex-minus-gf-minus-FBS. To wells provided with the Cambrex-minus-gf-minus-FBS, inserts were added containing alginic acid (AA) hydrogel particles plus 0, 5 or 10% FBS. The AA particles released the FBS into the media leading to increased cell growth.

DETAILED DESCRIPTION OF THE INVENTION

In one aspect, the invention is based on the discovery that biodegradable, bioactive polymers or hydrogels can be used to create wound dressings, implantable compositions, and coatings for medical devices that promote endogenous tissue restoration processes at a wound site. Allogenic or autologous precursor cells dispersed in a polymer or hydrogel matrix promote endogenous healing processes at the wound site by interaction with and secretion into the tissue surroundings of

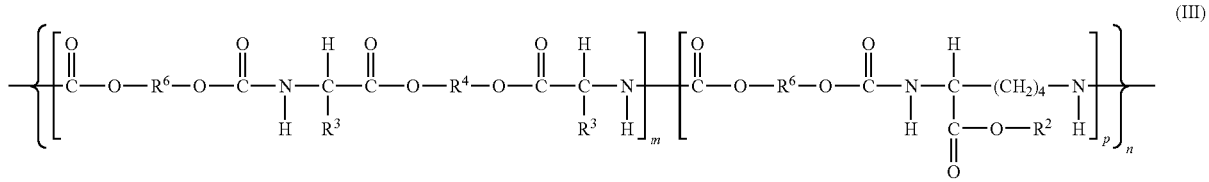

and wherein n ranges from about 5 to about 150, m ranges about 0.1 to about 0.9: p ranges from about 0.9 to about 0.1; wherein $R^2$ is hydrogen or $(C_6\text{-}C_{10})$aryl$(C_1\text{-}C_6)$alkyl or t-butyl or other protecting group; $R^3$ is selected from the group consisting of hydrogen, $(C_1\text{-}C_6)$alkyl, $(C_2\text{-}C_6)$alkenyl, $(C_2\text{-}C_6)$alkynyl and $(C_6\text{-}C_{10})$aryl$(C_1\text{-}C_6)$alkyl; and $R^4$ is selected from the group consisting of $(C_2\text{-}C_{20})$alkylene, $(C_2\text{-}C_{20})$alkenylene or $(C_2\text{-}C_{20})$alkyloxy$(C_2\text{-}C_{20})$alkylene, and bicyclic-fragments of 1,4:3,6-dianhydrohexitols of general formula a mixture of factors and cytokines that promote tissue restoration. In addition, the polymers can be loaded with various bioactive agents that either attract or hold the precursor cells within the polymer matrix or promote the natural healing process in a wound, such as a chronic wound. As the hydrogels or polymers biodegrade over time, released bioactive agents can either be absorbed into a target cell in a wound or lesion site to act intracellularly, or the bioactive agent can bind to a cell surface receptor molecule to elicit a cellular response without entering the cell. Depending upon the rate of biodegradation of the polymer or hydrogel selected, the tissue remodeling properties of the invention wound dressings, optionally implantable, will begin to take place even before biodegradation of the polymer.

Stem cells in embryonic tissues In general, human tissues have a very limited potential to regenerate. However, stem cells from embryos have the potential to form all adult tissues. Embryonic stem cells can be cultured to produce both a stable pluripotent cell population and its associated conditioned medium.

Stem cells in adult tissues Since the development of embryonic stem cell cultures, "stem cells" have been discovered to exist in many adult tissues. In fact these broadly labeled adult "stem cells" should more accurately be described as "precursor cells", consisting of multiple populations of cells, including tissue-specific progenitor cells, germ-layer lineage stem cells, and pluripotent stem cells.

Tissue-specific progenitor cells display various capacities for differentiation, ranging from unipotency (forming a single cell type) to multipotency (forming multiple cell types).

Germ-layer lineage stem cells can form a wider range of cell types than a progenitor cell. An individual germ-layer lineage stem cell can form all cell types within its respective germ-layer lineage (i.e., ectoderm, mesoderm, or endoderm). Pluripotent stem cells can form a wider range of cell types than a single germ-layer lineage stem cell. A single pluripotent stem cell can form cells belonging to all three germ layer lineages. Thus, pluripotent stem cells are clonal cells that self-renew as well as differentiate to regenerate adult tissues.

Both germ-layer lineage stem cells and pluripotent stem cells have extended capabilities for self-renewal, far surpassing the limited life span of progenitor cells.

A discussion follows of various categories of tissue wounds and lesions and the types of related precursor cells that have been identified as suitable for promoting repair and restoration of involved tissues at such sites. According to the invention, wound dressings containing the indicated type of precursor cells, or conditioned medium thereof, can be used for promoting tissue remodeling at the indicated tissue lesion sites.

Stem Cells in Adult Tissues—from Bone Marrow

Adult bone marrow-derived progenitor cells have traditionally been considered to be tissue-specific cells with limited capacity for differentiation. However, recent discoveries have demonstrated that, under the influence of appropriate cytokine molecules such marrow-derived progenitor cells actually possess the potential ability to regenerate cells of various different lineages. Thus the hypothesis that a common 'interchangeable' progenitor cell may exist within the bone marrow capable of regenerating and repairing tissues throughout the body has been confirmed in a few examples to date. This result has created the possibility of using bone marrow-derived stem cells as a source of cells and conditioned medium for therapeutic tissue repair and regeneration in various body sites.

Endothelia, And Associated Tissue

Bone Marrow-Derived Endothelial Progenitor Cells: Adult Neovascularization

Postnatal neovascularization is not restricted to angiogenesis, but also includes vasculogenesis. In the hematopoietic system the only long-term self-renewing cells in the stem and progenitor pool are the hematopoietic stem cells of the bone marrow. In response to vascular trauma and/or tissue ischemia, during adult vasculogenesis endothelial progenitor cells (EPCs), derived from the bone marrow stem cell pool, are recruited to the systemic circulation. From these progenitors, endothelial cell maturation and differentiation into arterial, venous, and lymphatic endothelium can occur, leading to either vascular repair or formation.

Epithelia

Stem Cells in the Eye

Limbal stem cells are essential for the maintenance of the corneal epithelium, and these cells are now used clinically for repair of severely damaged cornea.

Tooth Development & Repair

Future treatment could be based upon the discovery of dental epithelial stem cells in continuously growing teeth, such as impacted wisdom teeth in adults.

Lung Morphogenesis and Injury Repair

Lung development, as well as epithelial injury repair in the lung, is tightly coordinated by a fine balance between stimulatory versus inhibitory genes that appear to co-regulate the function of stem/progenitor cells in the lung. Use of activated lung stem/progenitor cells in invention implantable compositions may aid in ameliorating lung injury, augment lung repair and/or induce lung regeneration in both children and adults with intractable pulmonary insufficiency. Progenitor cells of glandular and myoepithelial lineages in the human adult female breast epithelium Phenotypically and behaviourally, progenitor (committed adult stem) cells of human breast epithelium have the potential to differentiate into either glandular or myoepithelial cells through various intermediary cells and may be used in invention implantable compositions for tissue restoration at lesion sites in such tissue.

Connective & Skeletal Tissues

Mesenchymal Stem Cells in Osteobiology and Applied Bone Regeneration.

Bone marrow contains a population of rare progenitor cells capable of differentiating into bone, cartilage, muscle, tendon, and other connective tissues. These cells are referred to as mesenchymal stem cells (MSCs) and can be used in the invention methods and devices to enhance tissue reformation in bone, cartilage, muscle, tendon, and other connective tissues.

Cardiac Muscle

Cardiac progenitor cells have defeated the dogma that myocyte regeneration cannot occur in the adult heart. Most importantly, primitive and progenitor cells have been identified in the human heart. For cardiomyocyte proliferation in damaged heart, the use of bone marrow-derived stem cells provides a less invasive source for cells useful in invention devices and compositions associated with to cardiovascular tissue engineering, such as heart valves, blood vessels, and myocardium. Additionally, early embryonic cells can be recruited to the myocardial lineage and used for such purposes in cardiac tissue restoration.

Bone

Ideally skeletal reconstruction depends on regeneration of normal tissues that result from initiation of progenitor cell activity. Basic requirements include a scaffold conducive to cell attachment and maintenance of cell function, together with a rich source of progenitor cells. In the latter respect, bone is a special case and there is a vast potential for regeneration from cells with stem cell characteristics. The development of osteoblasts, chondroblasts, adipoblasts, myoblasts, and fibroblasts has been shown to result from colonies derived from such single cells. In principle, these precursor cells may be used in the invention wound healing implantable compositions for regeneration of all tissues that these varieties of cells comprise: bone, cartilage, fat, muscle, tendons, and ligaments.

In particular, the repair of a fracture necessarily entails synthesis of osseous tissue requiring the transformation of undifferentiated osteochondral progenitor cells to mature osteoblasts and chondrocytes. It has been proposed that there are stem cells for all mesenchymal tissues, resident in bone marrow throughout life, that have a lineage comparable to that described for hematopoiesis. Marrow derived and periosteal derived progenitor cells have been shown to produce bone and cartilage in numerous in vivo and in vitro studies. For example, in an in vitro study of chondrogenesis, the marrow derived progenitor cells were shown to differentiate into their terminal phenotype, the hypertrophic chondrocyte.

Repair of Articular Cartilage

There is no natural repair mechanism to heal damaged or diseased cartilage. However, full-thickness defects involving the subchondral bone can be repaired with the use of pluripotent progenitor cells from bone marrow or from transplanted perichondrium or periosteum. The mechanism of fibrocartilaginous repair appears to be mediated by proliferation and differentiation of mesenchymal cells obtained from the bone marrow. Biologic grafts such as perichondrium have been successfully used to repair full-thickness defects, presumably because grafts of perichondrium contain progenitor cells that can differentiate into chondroblasts, and the like.

Stem Cells and Tissue Engineering: Prospects for Regenerating Tissues in Dental Practice Specific signal molecules have been identified that regulate the development of teeth and bones from progenitor cells. This information is already being used for generation of dentoalveolar tissues in vitro and in vivo. Future developments will be to grow new enamel, dentine, periodontal ligament, bone, or even whole new teeth in patients. It has been demonstrated that the potential for regeneration of the periodontium is highly dependent upon defect morphology and the availability of "progenitor cells."

Tissue Engineering of Ligament and Tendon Healing

Ligaments and tendons are bands of dense connective tissue that mediate normal joint movement and stability. Introduction of mesenchymal progenitor cells as a pluripotent cell source into the healing environment can be used to restore damage to ligaments and tendons.

Hair Cell Regeneration in the Inner Ear

Hearing and balance disorders caused by the loss of inner ear hair cells are a common problem encountered in otolaryngology-head and neck surgery. Current work is focused on the cellular progenitor source of new hair cells and the trigger mechanism responsible for inducing hair cell regeneration.

Neuronal

Brain Repair: Neurogenesis and Gliogenesis

Neural stem cells (NSCs) are subscribed extraordinary potential in repair of the damaged nervous system. However, the molecular identity of NSCs has not been fully established. Most NSC cultures contain large numbers of multipotent, bipotent, and lineage restricted neural progenitors—the majority of which appear to lose neurogenic potential after expansion. Thus, a single NSC is capable of generating various kinds of cells within the central nervous system (CNS), including neurons, astrocytes, and oligodendrocytes. Because of these characteristics, there is increasing interest in NSCs and neural progenitor cells for therapeutic applications in the damaged brain.

Major advances in the study of neural progenitor cells have resulted in rational approaches to the repair of the damaged nervous system using transplanted progenitor cells.

Role of Muller Glia in Neuroprotection and Regeneration in the Retina

The vertebrate retina is derived from paired evaginations from the neural tube in embryonic development and is initially produced by progenitor cells similar to those that generate the neurons and glia of other areas of the central nervous system.

Glial cells are thought to protect neurons from various neurological insults. When there is injury to retina, Muller cells, which are the predominant glial element in the retina, undergo significant morphological, cellular and molecular changes. Muller cells contact to endothelial cells to facilitate the neovascularization process during hypoxic conditions. Recent studies have pointed to a role of Muller cells in retinal regeneration after damage, dedifferentiating to progenitor cells and then giving rise to different neuronal cell types.

Enhanced Neurogenesis Following Stroke

Proliferation, migration, and maturation of neural precursors are affected by ischemia. There exists compelling evidence that neural precursors resident in the brain initiate a compensatory response to stroke, resulting in the production of new neurons.

Evidence for neuronal self-repair following insults to the adult brain has been scarce until very recently. Ischaemic insults have now been shown to trigger neurogenesis from neural stem cells or progenitor cells located in the dentate subgranular zone, the subventricular zone lining the lateral ventricle, and the posterior periventricle adjacent to the hippocampus (See K. S Aboody et al. *PNAS* (2002) 97(23): 12846-12851 and R-L. Zhao, *Experimental Neurology* (2002) 174(1):11-20)

Olfactory Ensheathing Cells: Their Potential use for Repairing the Injured Spinal Cord Intraspinal transplants (e.g., fetal neuronal cells, progenitor stem cells, and olfactory ensheathing cells) have been used to restore intraspinal circuitry or to serve as a "bridge" for damaged axons. Olfactory ensheathing cells (EC) from olfactory lamina propria in the nose are among the best transplants for "bridging" descending and ascending pathways in damaged spinal cord. In particular, assays of growth factor expression in cultured ECs have shown that ECs expressed nerve growth factor (NGF), brain derived neurotrophic factor (BDNF) and glial cell-line derived neurotrophic factor (GDNF). ELISA confirmed the intracellular presence of NGF and BDNF and showed that, compared to BDNF, about seven times as much NGF was secreted by ECs. RT-PCR analysis demonstrated expression of mRNA for NGF, BDNF, GDNF and neurturin (NTN). In addition, ECs also expressed the receptors trkB, GFRalpha-1 and GFRalpha-2. Thus, ECs express a number of growth factors and that BDNF in particular can act both in a paracrine and autocrine manner. (E. Woodhall et al, *Brain Res Mol Brain Res*. (2001) 88(1-2):203-13).

Neural Stem/Progenitor Cells During Demyelination: Repair Mechanisms in Multiple Sclerosis In recent years, it has become evident that the adult mammalian central nervous system (CNS) contains a population of neural stem cells (NSCs) described as immature, undifferentiated, multipotent cells, which may be recruited for repair in neurodegenerative and demyelinating diseases. Theses NSCs may give rise to oligodendrocyte progenitor cells (OPCs) and other myelinating cells.

As myelinating OPCs fail to differentiate in multiple sclerosis, emerging knowledge of the molecules involved in this maturation may help in the design of future stem cell-based treatment of demyelinating diseases, such as multiple sclerosis. Experimental studies indicate that transplanted neonatal OPCs can repopulate the large areas of demyelination characteristic of MS with much greater efficiency than endogenous OPCs.

Promotion of Recovery from Spinal Cord Injury

The implantation of embryonic stem cells for remyelinating damaged axons is proposed and in clinical trials in certain countries. Human neural stem cells can replace damaged cells and improve function in a mouse model of spinal cord injury When human neural stem cells were injected into the site of spinal cord contusion injury in mice, the human cells survived and engrafted extensively within the injured mouse spinal cord, with cells persisting 17 weeks after transplantation. The injected neural stem cells differentiated into neurons and formed synapses between neurons. The mice so treated showed evidence of recovering coordinated locomotor function and stepping ability 16 weeks after engraftment (B. J. Cummings, PNAS (2005) Online edition Sep. 19, 2005).

Visceral Organs

Liver Regeneration and Repair tem and progenitor cells for hepatocytes have been known for some years. Other, non-physiologic sources of cells for therapeutic needs are not limited to those that participate in physiological repair processes. Alternates include stem cells from other adult populations such as bone marrow stromal cells, from fetal liver tissue, or from ex vivo differentiation of embryonic stem cells. Isolated, cultured, and expanded ex vivo, fetal hepatoblasts and fetal hepatocytes were the first to be studied. It was presumed that these cells were already "committed" to an hepatic lineage, bidirectional in the case of hepatoblasts (i.e. toward both cholangiocytes and hepatocytes) and hepatocyte-committed in the case of fetal hepatocytes. Differentiation of mouse embryonic stem (ES) cells into mature hepatocytes has now been readily demonstrated by a number of groups.

The diseases which are potentially most likely to show real benefit from such a procedure include primary liver diseases or diseases where extra-hepatic manifestations arise from abnormal gene expression or defective protein production by the liver (Wilson's disease, alpha-1-antitrypsin deficiency, tyrosenemia type I, hyperlipidoses, and porphyria, metabolic deficiencies eg. Crigler-Najjar syndrome, familial hypercholesterolemia and amyloidosis, oxalosis and coagulation defects like hemophilia A, Factor IX deficiency. Acquired liver diseases, particularly acute failure secondary to toxic or viral injury, have been treated in limited clinical trials with fetal and adult hepatocytes. The efficacy of these treatments in helping patients to survive until a donor organ became available, with improvement of clinical measures such as hepatic encephalopathy and cerebral perfusion pressures, is promising (S. Sell, Cancer Research (1990), 50(13):3811-3815).

Kidney Regeneration and Repair

There are renal stem cells and progenitor cells.

Progenitor Cells in the Adult Pancreas: Certain Diabetics

The beta-cell mass in the adult pancreas possesses the ability to undergo limited regeneration following injury. Pancreatic beta-cell replacement represents an attractive approach for treatment of type 1 and insulin requiring type 2 diabetic patients. Identifying the progenitor cells involved in this process and understanding the mechanisms leading to their maturation will produce new treatment opportunities.

This prospect is currently restricted by the limited availability of donor cells. Recent developments, including beta-cell expansion by reversible immortalization and generation of beta cells by differentiation from embryonic and adult tissue progenitor cells, may provide abundant sources of cultured human beta cells. Such cells could be genetically modified, as well as encapsulated in semi-permeable membranes, to increase their resistance to beta-cell degenerative agents (in type 2 diabetics) and to recurring autoimmunity (in type 1 diabetics)

Autoimmune Disease

High Dose Chemotherapy and Autologous Hematopoietic Stem Cell Transplantation for Rheumatoid Arthritis A new treatment approach, involving intense immunosuppression and autologous hematopoietic stem cell transplantation (SCT), has emerged in recent years for the treatment of severe, refractory rheumatic autoimmune diseases including rheumatoid arthritis (RA). The rationale of this strategy is based on the concept of immunoablation by intense immunosuppression with subsequent regeneration of naive T lymphocytes derived from reinfused hematopoietic progenitor cells.

In one aspect, the invention describes wound dressings and implants that comprise (a) a bioabsorbable hydrogel or polymeric (polymer, copolymer or polymer alloy) carrier into which is dispersed, mixed, dissolved, homogenized, and/or covalently bound ("dispersed") (b) at least one allogenic or autologous precursor cells, conditioned medium produced by such cells, or a combination thereof, effective for promoting natural wound healing processes over days, weeks, or months. The invention wound dressings and implants of the present invention can be in any appropriate form into which the polymer matrix, including precursor cells or conditioned medium and other bioactive agents, can be formed with polymer technological processing methods.

Experimental evidence suggests that tissue remodeling is impaired in the elderly, who represent the largest cohort of patients in need of tissue remodeling therapy. Therefore, the age-related factors that impair tissue remodeling would also impair the activity of autologous precursor cells, such as various types of progenitor cells, retrieved from older patients and delivered to their wound or lesion.

These drawbacks can be overcome, according to the invention methods, by administering to such patients cell-free conditioned medium prepared by culturing isolated allogenic precursor cells obtained from young healthy individuals, and processing the conditioned medium to remove cells therefrom to yield a cell-free conditioned medium.

For example, when cell-free conditioned medium is prepared from either autologous or allogenic bone marrow, the bone marrow can optionally be filtered prior to placement in the growth medium to remove particles larger than about 300μ to about 200μ. Bone marrow cells can also be separated from the filtered ABM for growth leading to production of precursor cells. Usually the growth time required to move from bone marrow to a composition comprising only a few cells among which are one or a few precursor cells is about 7 to 10 days. The bone marrow-derived precursor cells can be isolated, and additionally grown in a suitable growth medium for a suitable period of time, for example, about 24 hours, for the cells to secrete into the growth medium a mixture of cytokines and other factors. The conditioned medium containing the mixture of cytokines, factors, and the like, can be collected through a filter selected to remove cells or processed to substantially remove cells to produce a cell-free medium. Suitable culture conditions for both cell growth steps are well known in the art. Similar (but not necessarily identical) methods can be used if the precursor cells are derived from other tissues.

Cell-free medium derived from growth in vitro of autologous or allogenic precursor cells, such as, but not limited to, those obtained from bone marrow, can be used in the place of conditioned medium derived from growth in culture of cells obtained from autologous bone marrow to deliver to the tissue of a patient the many angiogenic factors secreted by precursor cells that participate in tissue restoration. The invention cell-free medium is produced by culturing isolated allogenic or autologous progenitor cells under suitable conditions and for a time sufficient for the progenitor cells to secrete mixed secretion products into the conditioned medium. The conditioned medium is then processed to yield a cell-free medium containing the mixed secretion products. As with preparation of donor blood for transfusion, in which only the red cells are typed and cross-matched, the other cells administered, as well as the plasma, are administered without any typing. The incidence of serious allergic responses to any of these products is very low. The cell-free conditioned medium derived from cells of an allogenic or autologous source can be considered as free of allergens as serum or plasma obtained from various donors.

The cytokines remaining in the cell-free medium are relatively small molecules as compared with the size of proteins and, therefore, lack features that the mammalian body recognizes as non-self, leading to immune response. The size differential between cells and cytokines makes it convenient to remove the cells from the growth medium to yield the cell-free medium by filtering the growth medium or by centrifugation, for example for five minutes at 10 k×g. The cell-free medium may be further processed, such as by freezing or lyophilization and placed into small containers, to make handling, storage and distribution convenient. Those of skill in the art would understand that the frozen or lyophilized cell-free medium would be readily reconstituted for use by addition of such fluids as sterilized water, physiological saline, and the like, using the techniques know in the art as suitable for preparing other types of blood cells and blood products for administration to a patient.

The bone marrow (BM) is a natural source of a broad spectrum of cytokines (e.g., growth factors), various factors and cells that are involved in the control of angiogenic processes, which are referred to herein collectively as "mixed secretion products" for convenience. It is therefore believed that the intramyocardial injection of autologous (A) BM or bone marrow cells derived therefrom, by taking advantage of the natural ability of these cells to secrete many angiogenic factors in a time-appropriate manner, provides an optimal intervention for achieving therapeutic collateral development in ischemic myocardium.

When the conditioned medium is not prepared to be cell-free, for example when the precursor cells are autologous, the filtering step is omitted. Alternatively still, the isolated precursor cells can be loaded live into the hydrogel or polymer matrix in a suitable growth medium and the invention wound dressing can be placed into a site requiring tissue restoration to allow production in situ of mixed secretion products by the cells while the cells are sequestered within the polymer or hydrogel matrix. In any event, the precursor cells, if present, need to remain alive only transiently after placement of the wound dressing or coated device, only long enough for interaction with the surrounding tissue to call forth appropriate secretion products and begin the endogenous processes tissue remodeling. The exact period of time required for this therapeutic effect to take place will differ according to the type of precursor cell employed and the type of surrounding tissue into which the invention wound dressing or coated device is placed. However, in general, the in situ life span of the precursor cells will be in the range from 10 hours to 10 days.

An "effective amount" of precursor cells or conditioned medium containing mixed precursor cell-secretion products, as the term is used herein, means an amount sufficient to stimulate development of tissue remodeling in a wound or lesion site. The effective amount for any particular patient will be determined by a physician taking into account such factors as patient general health and age, severity of the condition being treated, body weight, and the like.

The discovery that the mixture of secretion products secreted by precursor cells into growth medium can influence and promote tissue restoration has lead to the conclusion that conditioned medium obtained from isolated autologous or allogenic precursor cells, as described herein, can be substituted for autologous precursor cells to produce tissue restoration effects. Moreover, the advantages of using allogenic donor-provided precursor cells to produce the therapeutic conditioned medium are several. First, an ischemic or older patient does not have to undergo anesthesia to obtain autologous precursor cells, such as can be obtained from bone marrow. Young healthy donors produce more vigorous precursor cells and, hence, use of allogenic cells or especially cell-free conditioned medium produced by allogenic precursor cells reduces the trauma to a patient of obtaining the cells used in the invention wound dressings and compositions. In addition, the wound healing composition can be produced in advance and stored for immediate use by a recipient patient. For example, the wound dressing composition containing cell-free conditioned medium from allogenic cells can be frozen to accommodate storage. Alternatively, the cell-free conditioned medium can be prepared as described herein and frozen or lyophilized for storage and then reconstituted for infusion or "loading" into the invention polymer or hydrogel dressings at the point of use.

In one embodiment, the invention provides bioactive wound dressings or device coatings are designed for implantation into an internal body site and comprise at least one layer of a bioabsorbable polymer that releases the dispersed precursor cells, conditioned medium, wound healing drug or bioactive agent over a considerable period of time, for example, over a period of twenty-four hours, about seven days, about thirty days, about ninety days, and about one hundred twenty days. A cross-linked poly(ester amide), polycaprolactone, or poly(ester urethane) as described herein can be used for this purpose so that the wound dressing is completely bioabsorbable. In this case, over time, the wound dressing will be re-absorbed by the body through natural enzymatic action and at a controlled rate dependent upon the selection of the polymer, allowing the re-established cell architecture to resume its natural function. Thus, the precursor cells or conditioned medium obtained from the precursor cells is released in situ as a result of biodegradation of the polymer carrier by enzymes found in mammalian subjects, such as humans.

The invention wound dressings and implantable compositions are also intended for use in veterinary treatment of wounds and lesions in of a variety of mammalian patients, such as pets (for example, cats, dogs, rabbits, ferrets), farm animals (for example, swine, horses, mules, dairy and meat cattle) and race horses.

Preferred additional bioactive agents for dispersion into and release from the biodegradable polymers used in the invention wound dressings and implantable compositions include anti-proliferants, rapamycin and any of its analogs or derivatives, paclitaxel or any of its taxene analogs or derivatives, everolimus, Sirolimus, tacrolimus, or any of its—limus named family of drugs, and statins such as simvastatin, atorvastatin, fluvastatin, pravastatin, lovastatin, rosuvastatin, geldanamycins, such as 17AAG (17-allylamino-17-demethoxygeldanamycin); Epothilone D and other epothilones, 17-dimethylaminoethylamino-17-demethoxygeldanamycin and other polyketide inhibitors of heat shock protein 90 (Hsp90), Cilostazol, and the like.

As used herein, "biodegradable" as used to describe the polymers and hydrogels used in the invention wound dressings, implantable compositions and device coating is capable of being broken down into innocuous and bioactive products in the normal functioning of the body. In one embodiment, the entire wound dressing or device coating is biodegradable. The preferred biodegradable, bioactive polymers have hydrolyzable ester linkages that provide the biodegradability, and are typically chain terminated predominantly with amino groups.

As used herein "dispersed" means a wound healing drug or mixture of drugs and/or one or more other bioactive agents as disclosed herein is dispersed, mixed, dissolved, homogenized, and/or covalently bound ("dispersed") in a polymer or hydrogel.

Polymers suitable for use in the practice of the invention can bear functionalities that allow for facile covalent attachment of bioactive agents to the polymer. For example, a polymer bearing carboxyl groups can readily react with a bioactive agent having an amino moiety, thereby covalently bonding the bioactive agent to the polymer via the resulting amide group. As will be described herein, the biodegradable, bioactive polymer and the bioactive agent can contain numerous complementary functional groups that can be used to covalently attach the bioactive agent to the biodegradable, bioactive polymer.

A polymer used in making an invention wound dressing or device coating, whether or not present in a formulation as described herein, whether or not linked to a bioactive agent as described herein, and whether or not intermixed with a bioactive agent as described herein, can also be used in medical therapy. For example, the polymer can be used in the manufacture of a medical device or a coating for at least a portion of an implantable medical or drug delivery device. Such implantable medical devices include, for example, orthopedic implants, such as artificial joints, artificial bones or intravertebral implants; bone pins and plates, surgical implants and wraps, implantable drug delivery devices, cardiovascular medical devices, stents, shunts, medical devices useful in angioplastic therapy, artificial heart valves, artificial by-passes, sutures, artificial arteries, vascular delivery, monitoring and treatment catheters, and adhesion barriers for local bioactive agent delivery systems.

As used herein, "bioactive" means the wound dressing or device coating contains a polymer having dispersed precursor cells and/or conditioned medium from such cells that play an active role in the endogenous healing processes at a wound site or site of device implant by holding the precursor cells or conditioned medium at the site of the wound or lesion for a period of time sufficient to allow the precursor cells and/or conditioned medium from growth of such cells to interact with surrounding tissue to affect tissue remodeling processes, while slowly releasing the precursor cells or drug or bioactive agent during biodegradation of the polymer and/or hydrogel contained therein. In addition, in certain embodiments the polymers disclosed herein (i.e., those having structural formulae (I-VIII and XI) may be bioactive upon enzymatic degradation, providing essential amino acids that nurture cells while the other breakdown products can be metabolized in the way that fatty acids and sugars are metabolized.

Bioactive agents contemplated for dispersion within the polymers and hydrogels used in the invention wound dressings and device coatings include agents that, when freed or eluted from the polymer or hydrogel during its degradation, promote endogenous production of a therapeutic natural wound healing agent, such as nitric oxide, which is endogenously produced by endothelial cells. Alternatively the bioactive agents released from the polymers during degradation may be directly active in promoting natural wound healing processes by endothelial cells. These bioactive agents can be any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such agents include, for example, aminoxyls, furoxans, nitrosothiols, nitrates and anthocyanins; nucleosides such as adenosine and nucleotides such as adenosine diphosphate (ADP) and adenosine triphosphate (ATP); neurotransmitter/neuromodulators such as acetylcholine and 5-hydroxytryptamine (serotonin/5-HT); histamine and catecholamines such as adrenalin and noradrenalin; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

Small proteinaceous motifs, such as the B domain of bacterial Protein A and the functionally equivalent region of Protein G, that are known to bind to, and thereby capture, such antibody molecules can be covalently attached by the Fc region to the polymers and will act as ligands to attach antibodies for use as capture antibodies to hold precursor cells or capture cells out of the patient's blood stream. Therefore, the antibody types that can be attached to polymer coatings using a Protein A or Protein G functional region are those that contain an Fc region. The capture antibodies will in turn bind to and hold precursor cells, such as progenitor cells, near the polymer surface while the precursor cells, which are preferably bathed in a growth medium within the polymer or hydrogel, secrete various factors and interact with other cells of the subject at the lesion site. In addition, one or more active agents contained in the wound dressing, such as the bradykinins, may activate the precursor cells.

For example, bioactive agents for attaching precursor cells or for capturing PECs from the subject's blood are monoclonal antibodies directed against a known precursor cell surface marker. For example, complementary determinants (CDs) that have been reported to decorate the surface of endothelial cells include CD31, CD34+, CD34−, CD102, CD105, CD106, CD109, CDw130, CD141, CD142, CD143, CD144, CDw145, CD146, CD147, and CD166. These cell surface markers can be of varying specificity and the degree of specificity for a particular cell/developmental type/stage is in many cases not fully characterized. In addition these cell marker molecules against which antibodies have been raised will overlap (in terms of antibody recognition) especially with CDs on cells of the same lineage: monocytes in the case of endothelial cells. Circulating endothelial progenitor cells are some way along the developmental pathway from (bone marrow) monocytes to mature endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of blood in the site into which the wound dressing is implanted. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies. However, it should be noted that access of the wound dressing to circulating blood may be minimal, especially in treatment of chronic wounds.

The following drugs and bioactive agents will be particularly effective for dispersion within the polymers used in making invention wound dressings, whether dispersed within a time release biodegradable hydrogel, as described herein, or a biodegradable polymer, for example, one having a chemical structure described by formulae I and III herein. The bioactive agents that are incorporated into the invention wound dressings, and device coatings, like the type of precursor cells, may differ depending upon the particular tissue type or tissue site under treatment.

In general, the suitable bioactive agents are not limited to, but include, various classes of compounds that facilitate or contribute to wound healing when presented in a time-release fashion to the wound or lesion surface. Such bioactive agents include wound-healing cells in addition to precursor cells, which can be protected, nurtured and delivered by the biodegradable polymer(s) and/or hydrogels in the invention wound dressings. Such additional wound healing cells include, for example, pericytes and endothelial cells, as well as inflammatory healing cells. To recruit such cells to the wound bed or lesion site, the wound dressings can include ligands for such cells, such as antibodies and smaller molecule ligands, that specifically bind to "cellular adhesion molecules" (CAMs). Exemplary ligands for wound healing cells include those that specifically bind to Intercellular adhesion molecules (ICAMs), such as ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD106 antigen)]; Neural cell adhesion molecules (NCAMs), such as NCAM-1 (CD56 antigen); or NCAM-2; Platelet endothelial cell adhesion molecules PECAMs, such as PECAM-1 (CD31 antigen); Leukocyte-endothelial cell adhesion molecules (ELAMs), such as LECAM-1; or LECAM-2 (CD62E antigen), and the like.].

These wound healing cells, for example, can be dispersed within a hydrogel loaded with a suitable growth medium for the cells. Synthetic tissue grafts, such as Apligraf® (Novartis), which is specifically formulated for healing of diabetic chronic wounds, can be supported by attachment to polymer layers in invention wound dressings.

In another aspect, the wound-healing bioactive agents include extra cellular matrix proteins, macromolecules that can be dispersed into the invention wound dressings or implants, e.g., attached either covalently or non covalently. Examples of useful extra-cellular matrix proteins include, for example, glycosaminoglycans, usually linked to proteins (proteoglycans), and fibrous proteins (e.g., collagen; elastin; fibronectins and laminin). Bio-mimics of extra-cellular proteins can also be used. These are usually non-human, but biocompatible, glycoproteins, such as alginates and chitin derivatives. Wound healing peptides that are specific fragments of such extra-cellular matrix proteins and/or their bio-mimics can also be used.

Proteinaceous growth factors are an additional category of wound healing bioactive agents suitable for incorporation into the various invention wound dressings described herein. For example, Platelet Derived Growth Factor-BB (PDGF-BB), Tumor Necrosis Factor-alpha (TNF-alpha), Epidermal Growth Factor (EGF), Keratinocyte Growth Factor (KGF), Thymosin B4; and, various angiogenic factors such as vascular Endothelial Growth Factors (VEGFs), Fibroblast Growth Factors (FGFs), Tumor Necrosis Factor-beta (TNF-beta), and Insulin-like Growth Factor-1 (IGF-1). Many of these proteinaceous growth factors are available commercially or can be produced recombinantly using techniques well known in the art.

Alternatively, expression systems comprising vectors, particularly adenovirus vectors, incorporating genes encoding such proteinaceous growth factors can be dispersed into the invention wound dressings for administration of the growth factors to the wound bed. For care of chronic wounds, the growth factors such as VEGFs, PDGFs, FGF, NGF, and evolutionary and functionally related biologics, and angiogenic enzymes, such as thrombin are preferred. For case of acute wounds, the cell recruitment biologics, such as therapeutic antibodies and cell receptor or receptor ligand molecules, and active fragments thereof, are preferred.

Drugs that enable healing are an additional category of wound healing bioactive agents suitable for dispersion into the various invention wound dressings, polymer implants and device coatings described herein. Such healing enabler drugs include, for example, antimicrobials and anti-inflammatory agents as well as certain healing promoters, such as, for example, vitamin A and synthetic inhibitors of lipid peroxidation.

A variety of antibiotics can be dispersed in the invention wound dressings, implants and implantable device coatings to indirectly promote natural healing processes by preventing or controlling infection. Suitable antibiotics include many classes, such as aminoglycoside antibiotics or quinolones or beta-lactams, such as cefalosporines, e.g., ciprofloxacin, gentamycin, tobramycin, erythromycin, vancomycin, oxacillin, cloxacillin, methicillin, lincomycin, ampicillin, and colistin. Suitable antibiotics have been described in the literature.

Suitable antimicrobials include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory agents useful for dispersion in polymers and/or hydrogels used in invention wound dressings, implants and device coatings, depending on the body site to be treated, include, e.g. analgesics (e.g., NSAIDS and salicyclates), steroids, antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference,* 2004 Edition. Specifically, the anti-inflammatory agent can include dexamethasone, which is chemically designated as (11 9, 16I)-9-fluro-11,17,21-trihydroxy-16-methylpregna-1,4-diene-3,20-dione. Alternatively, the anti-inflammatory agent can include sirolimus (rapamycin), which is a triene macrolide antibiotic isolated from *Steptomyces hygroscopicus*.

In certain embodiments of the invention, the bioactive agents are covalently bonded to the polymers used in the invention wound dressings, implants and device coatings. The following examples illustrate the ease with which certain categories of bioactive agents can be dispersed into the invention polymers. Aminoxyls contemplated for use as bioactive agents have the structure:

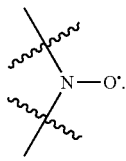

Exemplary aminoxyls include the following compounds:

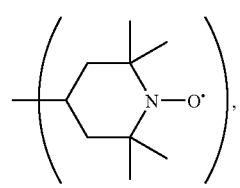

1

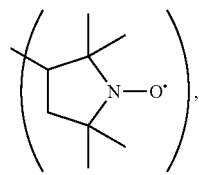

2

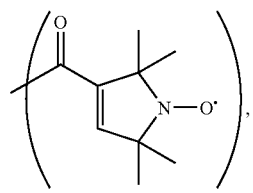

3

2,2,6,6-tetramethylpiperidine-1-oxy (1); 2,2,5,5-tetramethylpyrrolidine-1-oxy (2); and 2,2,5,5-tetramethylpyrroline-1-oxy-3-carbonyl (3). Further aminoxyls contemplated for use include 4-amino-2,2,6,6-tetramethylpiperidine-1-oxy (TEMPAMINE); 4-(N,N-dimethyl-N-hexadecyl)ammonium-2,2,6,6-tetramethylpiperidine-1-oxy, iodide (CAT16); 4-(N,N-dimethyl-N-(2-hydroxyethyl))ammonium-2,2,6,6-tetramethylpiperidine-1-oxy (TEMPO choline); 4-(N,N-dimethyl-N-(3-sulfopropyl)ammonium-2,2,6,6-tetramethylpiperidine-1-oxy; N-(4-(iodoacetyl)amino-2,2,6,6-tetramethylpiperidine-1-oxy(TEMPO 1A); N-(2,2,6,6-tetramethylpiperidine-1-oxy-4-yl)maleimide(TEMPO maleimide, MAL-6); and 4-trimethylammonium-2,2,6,6-tetramethylpiperidine-1-oxy, iodide (CAT 1); 3-amino-2,2,5,5- tetramethylpyrrolidine-1-oxy; and N-(3-(iodoacetyl)amino)-2,2,5,5-tetramethylpyrrolidine-1-oxy(PROXYL 1A); succinimidyl 2,2,5,5-tetramethyl-3-pyrroline-1-oxy-3-carboxylate and 2,2,5,5-tetramethyl-3-pyrroline-1-oxy-3-carboxylic acid, and the like.

Furoxans contemplated for use as bioactive agents have the structure:

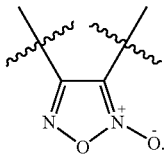

An exemplary furoxan is 4-phenyl-3-furoxancarbonitrile, as set forth below:

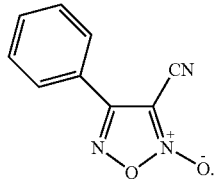

Nitrosothiols include compounds bearing the —S—N=O moiety, such as the exemplary nitrosothiol set forth below:

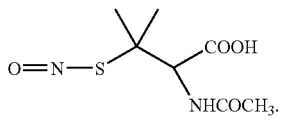

Anthocyanins are also contemplated for use as bioactive agents. Anthocyanins are glycosylated anthocyanidins and have the structure:

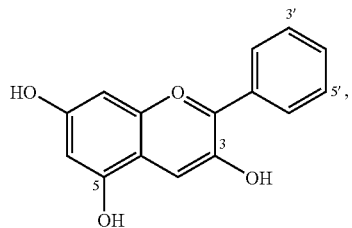

wherein the sugars are attached to the 3-hydroxy position. Anthocyanins are known to stimulate NO production in vivo and therefore are suitable for use as bioactive agents in the practice of the invention.

In further embodiments, the bioactive agent dispersed in the polymer is a ligand for attaching to or capturing progenitor endothelial cells floating within the blood stream within a blood vessel. In one example, the ligand is a "sticky" peptide or polypeptide, such as Protein A and Protein G. Protein A is a constituent of staphylococcus A bacteria that binds the Fc region of particular antibody or immunoglobulin molecules, and is used extensively to identify and isolate these molecules. For example the Protein A ligand can be or contain the amino acid sequence:

(SEQ ID NO: 1)
MTPAVTTYKLVINGKTLKGETTTKAVDAETAEKAFKQYANDNGVDGVWTY

DDATKTFTVTE or a functionally equivalent peptidic derivative thereof, such as, by way of an example, the functionally equivalent peptide having the amino acid sequence:

(SEQ ID NO: 2)
TYKLILNGKTLKGETTTEAVDAATAEKVFKQYANDNGVDGEWTYDDATKT

FTVTE

Protein G is a constituent of group G streptococci bacteria, and displays similar activity to Protein A, namely binding the Fc region of particular antibody or immunoglobulin molecules. For example, the Protein G ligand can be, or contain Protein G having an amino acid sequence:

(SEQ ID NO: 3)
MTPAVTTYKLVINGKTLKGETTTKAVDAETAEKAFKQYANDNGVDGVWTY

DDATKTFTVTE or a functionally equivalent peptidic derivative thereof, such as, by way of an example, the functionally equivalent peptide having the amino acid sequence:

(SEQ ID NO: 4)
TYKLILNGKTLKGETTTEAVDAATAEKVFKQYANDNGVDGEWTYDDATKT

FTVTE

Other bioactive peptides contemplated for dispersion in the polymers and/or hydrogels used in the invention wound dressings and device coatings include the bradykinins. Bradykinins are vasoactive nonapeptides formed by the action of proteases on kininogens, to produce the decapeptide kallidin (KRPPGFSPFR) (SEQ ID NO:5), which can undergo further C-terminal proteolytic cleavage to yield the bradykinin 1 nonapeptide: (KRPPGFSPF) (SEQ ID NO: 6), or N-terminal proteolytic cleavage to yield the bradykinin 2 nonapeptide: (RPPGFSPFR) (SEQ ID NO: 7). Bradykinins 1 and 2 are functionally distinct as agonists of specific bradykinin cell surface receptors B1 and B2 respectively: both kallidin and bradykinin 2 are natural ligands for the B2 receptor whereas their C-terminal metabolites (bradykinin 1 and the octapeptide RPPGFSPF (SEQ ID NO:8) respectively) are ligands for the B1 receptor. A portion of circulating bradykinin peptides can be subject to a further post-translational modification: hydroxylation of the second proline residue in the sequence (Pro3 to Hyp3 in the bradykinin 2 amino acid numbering). Bradykinins are very potent vasodilators, increasing permeability of post-capillary venules, and acting on endothelial cells to activate calmodulin and thereby nitric oxide synthase.

Bradykinin peptides are dispersed into the polymers used in the invention wound dressings by attachment at one end of the peptide. In general, the unattached end of the bradykinin extends freely from the polymer to contact endothelial cells at the lesion site, thereby activating the endothelial cells with which contact is made. Endothelial cells activated in this way activate further progenitor endothelial cells with which they come into contact, thereby causing a cascade of endothelial cell activation at the site of the injury that results in endogenous production of nitric oxide.

In a still further aspect, the bioactive agent can be a nucleoside, such as adenosine, which is also known to be a potent activator of endothelial cells to produce nitric oxide endogenously.

the necessity of prior modification. In addition, the PEAs preferred for use in the invention wound dressings and device coating display no hydrolytic degradation when tested in a saline (PBS) medium, but in an enzymatic solution, such as chymotrypsin or CT) a uniform and linear erosive behavior has been observed.

In one embodiment, the biodegradable polymer used is a PEA having a chemical structure described by structural formula (I),

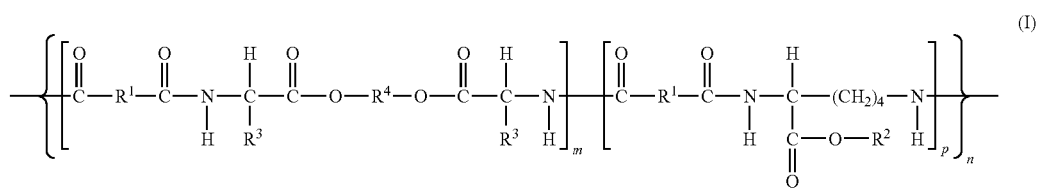

(I)

Polymers contemplated for use in forming the blood-compatible, hydrophilic polymer layer or coating in the invention wound dressings include polyesters, poly(amino acids), polyester amides, polyurethanes, or copolymers thereof. In particular, examples of biodegradable polyesters include poly($\alpha$-hydroxy $C_1$-$C_5$ alkyl carboxylic acids), e.g., polyglycolic acids, poly-L-lactides, and poly-D,L-lactides; poly-3-hydroxy butyrate; polyhydroxyvalerate; polycaprolactones, e.g., poly($\epsilon$-caprolactone); and modified poly($\alpha$-hydroxy-acid)homopolymers, e.g., homopolymers of the cyclic diester monomer, 3-(S)[alkyloxycarbonyl)methyl]-1,4-dioxane-2,5-dione which has the formula 4 where R is lower alkyl, depicted in Kimura, Y., "Biocompatible Polymers" in *Biomedical Applications of Polymeric Materials*, Tsuruta, T., et al, eds., CRC Press, 1993, page 179.

Examples of biodegradable copolymer polyesters useful in forming the blood-compatible, hydrophilic layer or coating include copolyester amides, copolyester urethanes, glycolide-lactide copolymers, glycolide-caprolactone copolymers, poly-3-hydroxy butyrate-valerate copolymers, and copolymers of the cyclic diester monomer, 3-(S)[(alkyloxycarbonyl)methyl]-1,4-dioxane-2,5-dione, with L-lactide. The glycolide-lactide copolymers include poly(glycolide-L-lactide) copolymers formed utilizing a monomer mole ratio of glycolic acid to L-lactic acid ranging from 5:95 to 95:5 and preferably a monomer mole ratio of glycolic acid to L-lactic acid ranging from 45:65 to 95:5. The glycolide-caprolactone copolymers include glycolide and $\epsilon$-caprolactone block copolymer, e.g., Monocryl or Poliglecaprone.

Further examples of polymers contemplated for use in the practice of the invention include polyester amides that have built-in functional groups on PEA backbones, and these built-in functional groups can react with other chemicals and lead to the incorporation of additional functional groups to expand the functionality of PEA further. Therefore, the PEAs used in the invention methods are ready for reaction with other chemicals having a hydrophilic structure to increase water solubility and with drugs and other bioactive agents, without and wherein n ranges from about 5 to about 150, m ranges about 0.1 to about 0.9: p ranges from about 0.9 to about 0.1; wherein $R^1$ is selected from the group consisting of ($C_2$-$C_{20}$) alkylene or ($C_2$-$C_{20}$)alkenylene; $R^2$ is hydrogen or ($C_6$-$C_{10}$) aryl($C_1$-$C_6$)alkyl or a protecting group; $R^3$ is selected from the group consisting of hydrogen, ($C_1$-$C_6$)alkyl, ($C_2$-$C_6$)alkenyl, ($C_2$-$C_6$)alkynyl and ($C_6$-$C_{10}$)aryl($C_1$-$C_6$)alkyl; and $R^4$ is selected from the group consisting of ($C_2$-$C_{20}$)alkylene, ($C_2$-$C_{20}$)alkenylene or ($C_2$-$C_{20}$)alkyloxy($C_2$-$C_{20}$)alkylene, and bicyclic-fragments of 1,4:3,6-dianhydrohexitols of general formula (II):

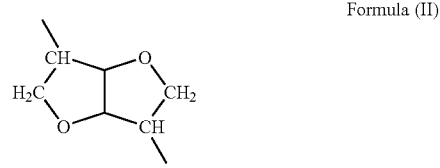

Formula (II)

except that for unsaturated polymers having the chemical structure of structural formula (I), $R^1$ and $R^4$ are selected from ($C_2$-$C_{20}$)alkylene and ($C_2$-$C_{20}$)alkenylene; wherein at least one of $R^1$ and $R^4$ is ($C_2$-$C_{20}$)alkenylene; n is about 5 to about 150; each $R^2$ is independently hydrogen, or ($C_6$-$C_{10}$)aryl($C_1$-$C_6$)alkyl; and each $R^3$ is independently hydrogen, ($C_1$-$C_6$) alkyl, ($C_2$-$C_6$)alkenyl, ($C_2$-$C_6$)alkynyl, or ($C_6$-$C_{10}$)aryl($C_1$-$C_6$)alkyl, or a PEUR having a chemical formula described by structural formula (III),

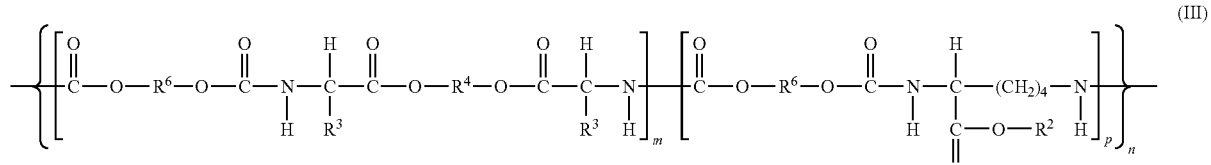

and wherein n ranges from about 5 to about 150, m ranges about 0.1 to about 0.9: p ranges from about 0.9 to about 0.1; wherein $R^2$ is hydrogen or $(C_6-C_{10})$aryl$(C_1-C_6)$alkyl or t-butyl or other protecting group; $R^3$ is independently selected from the group consisting of hydrogen, $(C_1-C_6)$alkyl, $(C_2-C_6)$alkenyl, $(C_2-C_6)$alkynyl and $(C_6-C_{10})$aryl$(C_1-C_6)$alkyl; and $R^4$ is selected from the group consisting of $(C_2-C_{20})$alkylene, $(C_2-C_{20})$alkenylene or $(C_2-C_{20})$alkyloxy $(C_2-C_{20})$alkylene, and bicyclic-fragments of 1,4:3,6-dianhydrohexitols of general formula (II); and $R^6$ is independently selected from $(C_2-C_{20})$alkylene, $(C_2-C_{20})$ alkenylene or alkyloxy, and bicyclic-fragments of 1,4:3,6-dianhydrohexitols of general formula (II), except that for unsaturated polymers having the structural formula (III) $R^6$ and $R^4$ are selected from $(C_2-C_{20})$alkylene and $(C_2-C_{20})$alkenylene; wherein at least one of $R^6$ and $R^4$ is $(C_2-C_{20})$alkenylene.

The bicyclic-fragments of 1,4:3,6-dianhydrohexitols can be derived from "sugar alcohols," such as D-glucitol, D-mannitol, and L-iditol. Useful protecting groups include t-butyl and others as is known in the art.

In one alternative, at least one of the α-amino acids used in fabrication of the invention polymers is a biological α-amino acid. For example, when the $R^3$s are $CH_2Ph$, the biological α amino acid used in synthesis is L-phenylalanine. In alternatives wherein the $R^3$s are $CH_2$—$CH(CH_3)_2$, the polymer contains the biological α amino acid, leucine. By varying the $R^3$s, other biological α-amino acids can also be used, e.g., glycine (when the $R^3$s are H), alanine (when the $R^3$s are $CH_3$), valine (when the $R^3$s are $CH(CH_3)_2$), isoleucine (when the $R^3$s are $CH(CH_3)$—$CH_2$—$CH_3$), phenylalanine (when the $R^3$s are $CH_2$—$C_6H_5$), lysine (when the $R^3$s are $(CH_2)_4$—$NH_2$); or methionine (when the $R^3$s or $R^4$s are —$(CH_2)_2SCH_3$), and mixtures thereof. In yet another embodiment, all of the various α-amino acids contained in the invention PEA and PEUR polymers are such biological α-amino acids, as described herein.

As used herein, the terms "amino acid", and "α-amino acid" mean a chemical compound containing an amino group, a carboxyl group and $R_3$ groups as defined herein. As used herein, the terms "biological amino acid" and "biological α-amino acid" mean the amino acid(s) used in synthesis is L-phenylalanine, leucine, glycine, alanine, valine, isoleucine, lysine, or methionine, or a mixture thereof.

The term "aryl" is used with reference to structural formulae herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to phenyl and naphthyl, and nitrophenyl.

The term "alkenylene" is used with reference to structural formulae herein to mean a divalent branched or unbranched hydrocarbon chain containing at least one unsaturated bond in the main chain or in a side chain.

The molecular weights and polydisperities herein are determined by gel permeation chromatograph using polystyrene standards. More particularly, number and weight average molecular weights ($M_n$ and $M_w$) are determined using a Model 510 gel permeation chromatograph (Water Associates, Inc., Milford, Mass.) equipped with a high-pressure liquid chromatographic pump, a Waters 486 UV detector and a Waters 2410 differential refractive index detector. Tetrahydrofuran (THF) is used as the eluent (1.0 mL/min). The polystyrene standards have a narrow molecular weight distribution.

Methods for making the polymers of structural formulas (I) and (III), containing an α-amino acid in the general formula are well known in the art. For example, for the embodiment of the polymer of structural formula (I) wherein R is incorporated into an α-amino acid, for polymer synthesis the α-amino acid can be converted into a bis-α-amino acid, for example, by condensing the α-amino acid with a diol HO—$R^2$—OH. As a result, ester fragments are formed. Then, the bis-α-amino acid is entered into a polycondensation reaction with a di-acid such as sebacic acid, to obtain the final polymer having both ester and amide bonds. Alternatively, instead of the di-acid, a di-acid derivative, e.g., di-para-nitrophenoxy di-acid, can also be used.

More particularly, synthesis of the unsaturated poly(ester-amide)s (UPEAs) useful as biodegradable polymers of the structural formula (I) as described above will be described, wherein

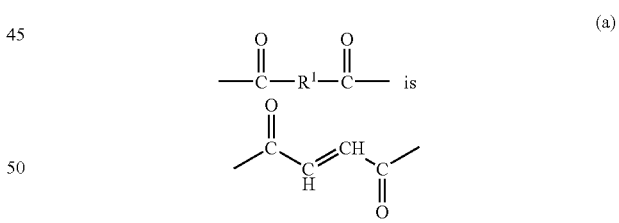

and/or (b) $R^4$ is —$CH_2$—$CH$=$CH$—$CH_2$—. In cases where (a) is present and (b) is not present, $R^4$ in (I) is —$C_4H_8$— or —$C_6H_{12}$—. In cases where (a) is not present and (b) is present, $R^1$ in (I) is —$C_4H_8$— or —$C_8H_{16}$—.

The UPEAs can be prepared by solution polycondensation of either (1) di-p-toluene sulfonic acid salt of diester of alpha-amino acid and unsaturated diol and di-p-nitrophenyl ester of saturated dicarboxylic acid or (2) di-p-toluene sulfonic acid salt of alpha-amino acid and saturated diol and di-nitrophenyl ester of unsaturated dicarboxylic acid or (3) di-p-toluene sulfonic acid salt of diester of alpha-amino acid and unsaturated diol and di-nitrophenyl ester of unsaturated dicarboxylic acid.

The aryl sulfonic acid salts are used instead of the free base because the aryl sulfonic acid group is a very good leaving group which can promote the condensation reaction to move to the right of the reaction equation so product is obtained in high yield and because the p-toluene sulfonic acid salts are known for use in synthesizing polymers containing amino acid residues.

The di-p-nitrophenyl esters of unsaturated dicarboxylic acid can be synthesized from p-nitrophenyl and unsaturated dicarboxylic acid chloride, e.g., by dissolving triethylamine and p-nitrophenyl in acetone and adding unsaturated dicarboxylic acid chloride dropwise with stirring at −78° C. and pouring into water to precipitate product. Suitable acid chlorides include fumaric, maleic, mesaconic, citraconic, glutaconic, itaconic, ethenyl-butane dioic and 2-propenyl-butanedioic acid chlorides. Additional compounds that can be used in the place of di-p-nitrophenyl esters of unsaturated dicarboxylic acid include those having structural formula (IV):

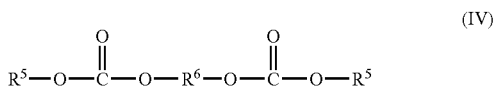

(IV)

wherein each $R^5$ is independently $(C_1-C_{10})$aryl optionally substituted with one or more nitro, cyano, halo, trifluoromethyl, or trifluoromethoxy; and $R^6$ is independently $(C_2-C_{20})$ alkylene or $(C_2-C_8)$alkyloxy$(C_2-C_{20})$alkylene.

The di-aryl sulfonic acid salts of diesters of alpha-amino acid and unsaturated diol can be prepared by admixing alpha-amino acid, e.g., p-aryl sulfonic acid monohydrate and saturated or unsaturated diol in toluene, heating to reflux temperature; until water evolution is minimal, then cooling. The unsaturated diols include, for example, 2-butene-1,4-diol and 1,18-octadec-9-en-diol.

Saturated di-p-nitrophenyl esters of dicarboxylic acid and saturated di-p-toluene sulfonic acid salts of bis-alpha-amino acid esters can be prepared as described in U.S. Pat. No. 6,503,538 B1.

Synthesis the unsaturated poly(ester-amide)s (UPEAs) useful as biodegradable polymers of the structural formula (I) as described above will now be described. Unsaturated compounds having the structural formula (I) can be made in similar fashion to the compound (VII) of U.S. Pat. No. 6,503, 538 B1, except that $R^4$ of (III) of U.S. Pat. No. 6,503,535 and/or $R^1$ of (V) of U.S. Pat. No. 6,503,538 is $C_2-C_{20}$ alkenylene as described above. The reaction is carried out, for example, by adding dry triethylamine to a mixture of said (III) and (IV) of U.S. Pat. No. 6,503,538 and said (V) in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30° C. under reduced pressure and then purifying up to negative test on p-nitrophenyl and p-toluene sulfonic acid. A preferred reactant (IV) is p-toluene sulfonic acid salt of benzyl ester. The benzyl ester protecting group is preferably removed to confer biodegradability, but it should not be removed by hydrogenolysis as in Example 22 of U.S. Pat. No. 6,503,538 because hydrogenolysis would saturate the desired double bonds; rather the benzyl ester group should be converted to an acid group by a method that would preserve unsaturation, e.g., by treatment with fluoroacetic acid or gaseous HF. Alternatively, the lysine reactant (IV) can be protected by a protecting group different from benzyl which can be readily removed in the finished product while preserving unsaturation, e.g., the lysine reactant can be protected with t-butyl (i.e., the reactant can be t-butyl ester of lysine) and the t-butyl can be converted to H while preserving unsaturation by treatment of the unsaturated product (I) with dilute acid.

A working example of a saturated compound having structural formula (I) is provided by substituting p-toluene sulfonic acid salt of L-phenylalanine 2-butene-1,4-diester for (III) in Example 1 of U.S. Pat. No. 6,503,538 or by substituting di-p-nitrophenyl fumarate for (V) in Example 1 of U.S. Pat. No. 6,503,538 or by substituting p-toluene sulfonic acid salt of L-phenylalanine 2-butene-1,4-diester for III in Example 1 of U.S. Pat. No. 6,503,538 and also substituting de-p-nitrophenyl fumarate for (V) in Example 1 of U.S. Pat. No. 6,503,538.

In unsaturated compounds having structural formula (I), the following hold: Aminoxyl radical e.g., 4-amino TEMPO can be attached using carbonyldiimidazol as a condensing agent. Bioactive agents, additional bioactive agents and wound-healing drugs, and the like, as described herein, can be attached via the double bond functionality. Hydrophilicity can be imparted by bonding to poly(ethylene glycol) diacrylate.

The biodegradable polymers and copolymers preferably have weight average molecular weights ranging from 10,000 to 300,000; these polymers and copolymers typically have inherent viscosities at 25° C., determined by standard viscosimetric methods, ranging from 0.3 to 4.0, preferably ranging from 0.5 to 3.5.

In yet another aspect, polymers contemplated for use in forming the invention wound healing dressings, implants and devices include those set forth in U.S. Pat. Nos. 5,516,881; 6,338,047; 6,476,204; 6,503,538; and in U.S. application Ser. Nos. 10/096,435; 10/101,408; 10/143,572; and 10/194,965.

In this embodiment, the biodegradable polymers and copolymers may contain up to two amino acids, such as biological amino acids, and preferably have weight average molecular weights ranging from 10,000 to 125,000; these polymers and copolymers typically have inherent viscosities at 25° C., determined by standard viscosimetric methods, ranging from 0.3 to 4.0, preferably ranging from 0.5 to 3.5.

Such poly(caprolactones) contemplated for use have an exemplary structural formula (V) as follows:

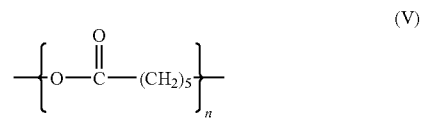

(V)

Poly(glycolides) contemplated for use have an exemplary structural formula (VI) as follows:

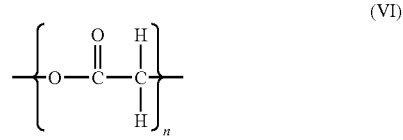

(VI)

Poly(lactides) contemplated for use have an exemplary structural formula (VII) as follows:

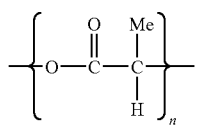
(VII)

An exemplary synthesis of a suitable poly(lactide-co-ε-caprolactone) including an aminoxyl moiety is set forth as follows. The first step involves the copolymerization of lactide and ε-caprolactone in the presence of benzyl alcohol using stannous octoate as the catalyst to form a polymer of structural formula (VIII).

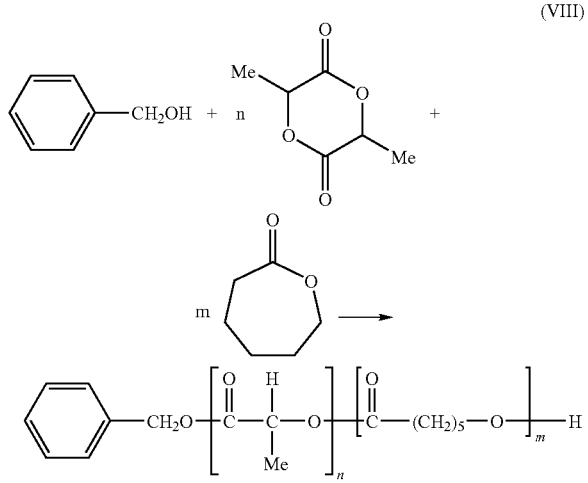
(VIII)

The hydroxy terminated polymer chains can then be capped with maleic anhydride to form polymer chains having structural formula (IX):

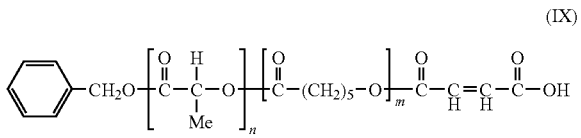
(IX)

At this point, 4-amino-2,2,6,6-tetramethylpiperidine-1-oxy can be reacted with the carboxylic end group to covalently attach the aminoxyl moiety to the copolymer via the amide bond which results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

Polymers contemplated for use in the practice of the invention can be synthesized by a variety of methods well known in the art. For example, tributyltin (IV) catalysts are commonly used to form polyesters such as poly(caprolactone), poly(glycolide), poly(lactide), and the like. However, it is understood that a wide variety of catalysts can be used to form polymers suitable for use in the practice of the invention.

The precursor cells are dispersed within the polymer matrix without direct chemical linkage to the polymer carrier, although it is contemplated that the precursor cells may be held within the polymer by a capture ligand, such as an antibody that binds to a cell surface marker, as described herein. However one or more bioactive agent can be covalently bound to the biodegradable, bioactive polymers via a wide variety of suitable functional groups. For example, when the biodegradable, bioactive polymer is a polyester, the carboxyl group chain end can be used to react with a complimentary moiety on the bioactive agent, such as hydroxy, amino, thio, and the like. A wide variety of suitable reagents and reaction conditions are disclosed, e.g., in *Advanced Organic Chemistry, Reactions, Mechanisms, and Structure*, Fifth Edition, (2001); and *Comprehensive Organic Transformations*, Second Edition, Larock (1999).

In other embodiments, a bioactive agent can be linked to any of the polymers of structures (I) and (III) through an amide, ester, ether, amino, ketone, thioether, sulfinyl, sulfonyl, disulfide, and the like, or a direct linkage. Such a linkage can be formed from suitably functionalized starting materials using synthetic procedures that are known in the art.

In one embodiment of the present invention, a polymer can be linked to the bioactive agent via a carboxyl group (e.g., COOH) of the polymer. Specifically, a compound of structures (I) and (III) can react with an amino functional group of a bioactive agent or a hydroxyl functional group of a bioactive agent to provide a biodegradable, bioactive polymer having a bioactive agent attached via an amide linkage or carboxylic ester linkage, respectively. In another embodiment, the carboxyl group of the polymer can be transformed into an acyl halide, acyl anhydride/"mixed" anhydride, or active ester.

Alternatively, the bioactive agent may be attached to the polymer via a linker. Indeed, to improve surface hydrophobicity of the biodegradable, bioactive polymer, to improve accessibility of the biodegradable, bioactive polymer towards enzyme activation, and to improve the release profile of the biodegradable, bioactive polymer, a linker may be utilized to indirectly attach the bioactive agent to the biodegradable, bioactive polymer. In certain embodiments, the linker compounds include poly(ethylene glycol) having a molecular weight (MW) of about 44 to about 10,000, preferably 44 to 2000; amino acids, such as serine; polypeptides with repeat units from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is $(C_1-C_{24})$alkyl, $(C_2-C_{24})$ alkenyl, $(C_2-C_{24})$alkynyl, $(C_3-C_8)$cycloalkyl, or $(C_6-C_{10})$ aryl, and W and Q are each independently —N(R)C(=O)—, —C(=O)N(R)—, —OC(=O)—, —C(=O)O—, —O—, —S—, —S(O)—, —S(O)$_2$—, —S—S—, —N(R)—, —C(=O)—, wherein each R is independently H or $(C_1-C_6)$ alkyl.

Polymers contemplated for use in the practice of the invention can be synthesized by a variety of methods well known in the art. For example, tributyltin (IV) catalysts are commonly used to form polyesters such as poly(caprolactone), poly(glycolide), poly(lactide), and the like. However, it is understood that a wide variety of catalysts can be used to form polymers suitable for use in the practice of the invention.

In certain embodiments, the bioactive agent can be covalently bound to the biodegradable, bioactive polymers via a wide variety of suitable functional groups. For example, when the biodegradable, bioactive polymer is a polyester, the carboxyl group chain end can be used to react with a complimentary moiety on the bioactive agent, such as hydroxy, amino, thio, and the like. A wide variety of suitable reagents and reaction conditions are disclosed, e.g., in *Advanced Organic Chemistry, Reactions, Mechanisms, and Structure*, Fifth Edition, (2001); and *Comprehensive Organic Transformations*, Second Edition, Larock (1999).

In other embodiments, precursor cells and bioactive agents can be dispersed into the polymer by "loading" onto the polymer without formation of a chemical bond or the bioactive agent can be linked to any of functional group in the polymers, such as an amide, ester, ether, amino, ketone, thioether, sulfinyl, sulfonyl, disulfide, and the like, to form a direct linkage. Such a linkage can be formed from suitably functionalized starting materials using synthetic procedures that are known in the art.

Alternatively still, the bioactive agent may be attached to the polymer via a linker. Indeed, to improve surface hydrophobicity of the biodegradable, bioactive polymer, to improve accessibility of the biodegradable, bioactive polymer towards enzyme activation, and to improve the release profile of the biodegradable, bioactive polymer, a linker may be utilized to indirectly attach the bioactive agent to the biodegradable, bioactive polymer. In certain embodiments, the linker compounds include poly(ethylene glycol) having a molecular weight (MW) of about 44 to about 10,000, preferably 44 to 2000; amino acids, such as serine; polypeptides with repeat units from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is $(C_1-C_{24})$alkyl, $(C_2-C_{24})$alkenyl, $(C_2-C_{24})$alkynyl, $(C_3-C_8)$cycloalkyl, or $(C_6-C_{10})$aryl, and W and Q are each independently —N(R)C(=O)—, —C(=O)N(R)—, —OC(=O)—, —C(=O)O, —O—, —S—, —S(O), —S(O)$_2$—, —S—S—, —N(R)—, —C(=O)—, wherein each R is independently H or $(C_1-C_6)$alkyl.

As used herein, the term "alkyl" refers to a straight or branched chain hydrocarbon group including methyl, ethyl, n-propyl, isopropyl, n-butyl, isobutyl, tert-butyl, n-hexyl, and the like.

As used herein, "alkenyl" refers to straight or branched chain hydrocarbyl groups having one or more carbon-carbon double bonds.

As used herein, "alkynyl" refers to straight or branched chain hydrocarbyl groups having at least one carbon-carbon triple bond.

As used herein, "aryl" refers to aromatic groups having in the range of 6 up to 14 carbon atoms.

In certain embodiments, the linker may be a polypeptide having from about 2 up to about 25 amino acids. Suitable peptides contemplated for use include poly-L-lysine, poly-L-glutamic acid, poly-L-aspartic acid, poly-L-histidine, poly-L-ornithine, poly-L-threonine, poly-L-tyrosine, poly-L-leucine, poly-L-lysine-L-phenylalanine, poly-L-arginine, poly-L-lysine-L-tyrosine, and the like.

The linker can be attached first to the polymer or to the bioactive agent. During synthesis of polymers containing bioactive agents indirectly attached via a linker, the linker can be either in unprotected form or protected from, using a variety of protecting groups well known to those skilled in the art.

In the case of a protected linker, the unprotected end of the linker can first be attached to the polymer or the bioactive agent. The protecting group can then be de-protected using Pd/H$_2$ hydrogenolysis, mild acid or base hydrolysis, or any other common de-protection method that are known in the art.

The de-protected linker can then be attached to the bioactive agent. An example using poly(ethylene glycol) as the linker is shown in Scheme 1.

Scheme 1

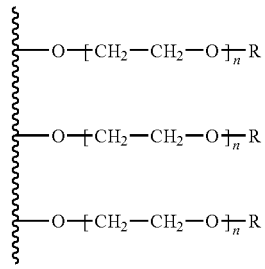

Poly(ethylene glycol) employed as the linker between polymer and drug/biologic.

wherein ∿∿∿ represents the polymer;

R can be either a drug or bioactive agent; and n can range from 1 to 200; preferable from 1 to 50.

An exemplary synthesis of a biodegradable, bioactive polymer according to the invention (wherein the bioactive agent is an aminoxyl) is set forth as follows.

A polyester can be reacted with an aminoxyl, e.g., 4-amino-2,2,6,6-tetramethylpiperidine-1-oxy, in the presence of N,N'-carbonyl diimidazole to replace the hydroxyl moiety in the carboxyl group at the chain end of the polyester with imino linked to aminoxyl-containing radical, so that the imino moiety covalently bonds to the carbon of the carbonyl residue of the carboxyl group. The N,N'-carbonyl diimidazole converts the hydroxyl moiety in the carboxyl group at the chain end of the polyester into an intermediate product moiety which will react with the aminoxyl, e.g., 4-amino-2,2,6, 6-tetramethylpiperidine-1-oxy. The aminoxyl reactant is typically used in a mole ratio of reactant to polyester ranging from 1:1 to 100:1. The mole ratio of N,N'-carbonyl diimidazole to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve; this information is normally available from the manufacturer of the polyester. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or DMSO at room temperature suitably dissolves the polyester. When the polyester is a poly-L-lactic acid, a poly-DL-lactic acid or a poly(glycolide-L-lactide) (having a monomer mole ratio of glycolic acid to L-lactic acid 50:50 or less than 50:50), tetrahydrofuran, methylene chloride and chloroform at room temperature to 50° C. suitably dissolve the polyester.

In another aspect, the biodegradable polymers or hydrogels can be coated onto the surface of a medical device, in many ways, such as dip-coating, spray-coating, ionic deposition, and the like, as is well known in the art, prior to loading with the precursor cells. In coating a porous surface of a medical device, care must be taken not to occlude the pores, which are needed to allow access and migration of cells, factors, and the like, from the surface of the device to the interior of the device, for example endothelial cells and other blood factors that participate in the natural biological process of wound healing and tissue reconstruction.

The medical device can be formed of any suitable substance, such as is known in the art. For example, the medical device can be formed from a bioceramic, such as a porous calcium phosphate cement or implantable object made therefrom, or a biocompatible metal, such as stainless steel, tantalum, nitinol, elgiloy, and the like, and suitable combinations thereof.

In another embodiment, the medical device can itself be substantially biodegradable, being made of cross-linkable "star structure polymers", or dendrimers, which are well known to those skilled in the art. In one aspect, the medical device is formed from biodegradable cross-linked poly(ester amide), polycaprolactone, or poly(ester urethane) as described herein.

Polymer/Bioactive Agent Linkage

In one embodiment, the polymers used to make the wound dressings and device coverings as described herein have one or more bioactive agents that promote natural wound healing directly linked to the polymer. The residues of the polymer can be linked to the residues of the one or more bioactive agents. For example, one residue of the polymer can be directly linked to one residue of the bioactive agent. The polymer and the bioactive agent can each have one open valence. Alternatively, more than one bioactive agent, or a mixture of bioactive agents, that promote natural re-endothelialization of vessels can be directly linked to the polymer. However, since the residue of each bioactive agent can be linked to a corresponding residue of the polymer, the number of residues of the one or more bioactive agents can correspond to the number of open valences on the residue of the polymer.

As used herein, a "residue of a polymer" refers to a radical of a polymer having one or more open valences. Any synthetically feasible atom, atoms, or functional group of the polymer (e.g., on the polymer backbone or pendant group) of the present invention can be removed to provide the open valence, provided bioactivity is substantially retained when the radical is attached to a residue of a bioactive agent. Additionally, any synthetically feasible functional group (e.g., carboxyl) can be created on the polymer (e.g., on the polymer backbone or pendant group) to provide the open valence, provided bioactivity is substantially retained when the radical is attached to a residue of a bioactive agent. Based on the linkage that is desired, those skilled in the art can select suitably functionalized starting materials that can be derived from the polymer of the present invention using procedures that are known in the art.

As used herein, a "residue of a compound of structural formula (*)" refers to a radical of a compound of formula s (I, III, and V-IX) having one or more open valences. Any synthetically feasible atom, atoms, or functional group of the compound of formulas (I-X) (e.g., on the polymer backbone or pendant group) can be removed to provide the open valence, provided bioactivity is substantially retained when the radical is attached to a residue of a bioactive agent. Additionally, any synthetically feasible functional group (e.g., carboxyl) can be created on the compound of formulas (I, III, and V-IX) (e.g., on the polymer backbone or pendant group) to provide the open valance, provided bioactivity is substantially retained when the radical is attached to a residue of a bioactive agent. Based on the linkage that is desired, those skilled in the art can select suitably functionalized starting materials that can be derived from the compound of formulas (I, III, and V-IX) using procedures that are known in the art.

For example, the residue of a bioactive agent can be linked to the residue of a compound of structural formula (I, III, and V-IX) through an amide (e.g., —N(R)C(=O)— or —C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or ($C_1$-$C_6$)alkyl. Such a linkage can be formed from suitably functionalized starting materials using synthetic procedures that are known in the art. Based on the linkage that is desired, those skilled in the art can select suitably functional starting material that can be derived from a residue of a compound of structural formula (I, III, and V-IX) and from a given residue of a bioactive agent using procedures that are known in the art. The residue of the bioactive agent can be linked to any synthetically feasible position on the residue of a compound of structural formula (I, III, and V-IX). Additionally, the invention also provides compounds having more than one residue of a bioactive agent or bioactive agents directly linked to a compound of structural formula (I, III, and V-IX).

The number of bioactive agents that can be linked to the polymer can typically depend upon the molecular weight of the polymer. For example, for a compound of structural formula (I), wherein n is about 50 to about 150, up to about 300 bioactive agents (i.e., residues thereof) can be directly linked to the polymer (i.e., residue thereof) by reacting the bioactive agent with end groups of the polymer. In unsaturated polymers, the bioactive agents can also be reacted with double (or triple) bonds in the polymer.

Hydrogels for use in Wound Dressings

Non-stick wound healing dressings and non-stick layers used in the invention wound-healing dressings and implantable cell or conditioned medium delivery compositions comprise a biodegradable hydrogel. Although any biodegradable hydrogel known in the art that can be loaded with precursor cells as described herein, wound healing drugs or bioactive agents for in situ delivery can be used for this purpose, preferred hydrogels have both hydrophobic and hydrophilic components and form a one-phase crosslinked polymer network structure by free radical polymerization. Such hydrogels effectively accommodate precursor cells as well as hydrophobic drugs (as well as hydrophilic drugs) and hydrogels with hydrophobic and hydrophilic components have the advantage of maintaining structural integrity for relatively longer periods of time and having increased mechanical strength compared to totally hydrophilic-based hydrogels. Due to its non-stick nature, the hydrogel layer can be placed directly into the wound bed or lesion to deliver its load of precursor cells or conditioned medium in situ and can be removed without damage to the developing cell architecture in the wound bed.

In one aspect, such a hydrogel is formed from a hydrogel-forming system that comprises from 0.01 to 99.99% by weight, for example, from 95% to 5%, by weight of (A), wherein (A) is a hydrophobic macromer with unsaturated group terminated ends, and from 99.99 to 0.01% by weight, for example, from 5% to 95%, by weight of (B), wherein (B) is a hydrophilic polysaccharide containing hydroxyl groups that are reacted with the unsaturated groups of the hydrophobic macromer. The total of the percentages of (A) and (B) is 100%. The hydrophobic macromer is biodegradable and is readily prepared by reacting diol—obtained by converting hydroxyls of terminal carboxylic acid groups of poly(lactic acid) to aminoethanol groups—with the unsaturated group-introducing compound.

Preferably, the hydrophilic polymer is dextran wherein one or more hydroxyls in a glucose unit of the dextran are reacted with the unsaturated group-introducing compound. In one case, the hydrophilic polymer can be dextran-maleic acid monoester as described in PCT/US99/18818.

A precursor cell, conditioned medium, wound-healing bioactive agent or drug, as described herein, can be loaded into (i.e., dispersed in) the hydrogel by a number of means depending on the molecular weight of the cells, agents or drug. For example, a drug of weight average molecular weight ranging from 200 to 1,000, as exemplified by indomethacin, can be entrapped in the three dimensional crosslinked polymer network for controlled release therefrom. Alternatively, a water-soluble macromolecule of weight average molecular weight ranging from 1,000 to 10,000, e.g., a polypeptide, as exemplified by insulin, can be entrapped in the three dimensional crosslinked polymer network for controlled release therefrom. In still another example, a precursor cell, e.g., weighing in the femtogram range, can be entrapped in the three dimensional crosslinked polymer network for controlled release therefrom.

The term "hydrogel" is used herein to mean a polymeric material that exhibits the ability to swell in water or other aqueous solution and to retain a significant portion of the aqueous solution within its structure without dissolving. Thus the hydrogels described herein are particularly suitable for loading of precursor cells in growth medium or for loading with conditioned medium, such as cell-free conditioned medium.

In certain embodiments, the biodegradable hydrogel used in the invention methods and devices is a hydrogel formed from a hydrogel forming system containing at least one biodegradable component, i.e., component that is degraded by water and/or by enzymes found in wounds and lesions of mammalian patients, such as humans and other animals.

The term "crosslinked polymer network structure" is used herein to mean an interconnected structure where crosslinks are formed between hydrophobic molecules, between hydrophilic molecules and between hydrophobic molecules and hydrophilic molecules.

The term "photocrosslinking" is used herein to mean causing vinyl bonds in the initiator to break and other vinyl bonds to form crosslinks by the application of radiant energy.

The term "macromer" is used herein to mean a monomer having a weight average molecular weight ranging from 500 to 80,000.

The term "unsaturated group-introducing compound" as used herein with respect to hydrogels means a compound that reacts with an hydroxyl group and provides a pendant or end group containing an unsaturated group, e.g., a pendant group with a vinyl group at its end.

The weight average molecular weights and number average molecular weights herein are determined by gel permeation chromatography.

A detailed description of such biodegradable hydrogels and their methods of preparation are described in U.S. Pat. Nos. 6,388,047 and 6,583,219.

Suitable compounds for use as the hydrophobic macromer (A) in the preparation of biodegradable hydrogels are readily obtained by converting the end groups of a starting material macromer to groups with terminal hydroxyl group if such are not already present as end groups, i.e., to provide a diol, and reacting the terminal hydroxyls with an unsaturated group-introducing compound to provide terminal unsaturated groups, e.g., vinyl groups, on the macromer. The starting material macromer preferably has a weight average molecular weight ranging up from 500 to 20,000, such as the aliphatic polyester poly(lactic acid) having a weight average molecular weight ranging from 600 to 8,000, e.g., 600 to 1,000 or 6,500 to 8,000, e.g., poly-D-,L-lactic acid (sometimes denoted PDLLA). Poly-D,L-lactic acid has widely been used as a biodegradable hydrophobic polymeric material due to its combination of biodegradability, biocompatibility, and adequate mechanical strength. The degradation of poly-D,L-lactic acid in vivo is well understood and the degradation products are natural metabolites that can be readily eliminated by the human body. Other starting material macromers that can be used include, for example, other aliphatic polyesters, such as poly(glycolic acid), poly(epsilon-caprolactone), poly(glycolide-co-lactide), poly(lactide-epsilon-caprolactone), polycaprolactone diols (e.g., with $M_n$ equal to 530, 1250 or 2000), polycaprolactone triols (e.g., with $M_n$ equal to 300 or 900), or any synthetic biodegradable macromer having one carboxyl end group and one hydroxyl end group, carboxyl groups at both ends, or hydroxyl groups at both ends.

Reaction of a diol with the unsaturated group-introducing compound provides a hydrophobic polymer with unsaturated end groups. The unsaturated group-introducing compound can be, for example, acryloyl chloride, methacryloyl chloride, acrylic acid, methacrylic acid, or isocyanate having unsaturated, e.g., vinyl, group at one end of the molecule, e.g., allyl isocyanate or isocyanatoethyl methacrylate. Vinyl terminated hydrophobic macromer A can be prepared from poly-D,L-lactic acid with mers ranging from 8 to 120.

The hydrophilic polymer (B) is a polysaccharide derivative. Suitable polysaccharides useful for preparing (B) have hydroxy functional pendant groups and include, for example, dextran, inulin, starch, cellulose, pullan, levan, mannan, chitin, xylan, pectin, glucuronan, laminarin, galactomannan, amylose, amylopectin, and phytoglucans. These polysaccharides have multiple hydroxy functional groups that permit the production of a three-dimensional network. The named polysaccharides are inexpensive. Dextran, which is the preferred polysaccharide starting material, is one of the most abundant naturally occurring biodegradable polymers. It is susceptible to enzymatic digestion in the body and consists mainly of (1→6) alpha-D-glucoside linkages with about 5-10% of (1→3) alpha-linked branching. It contains three hydroxyl groups per glucose repeating unit and therefore mediates formation of a crosslinked polymer network. Preferably, the dextran starting material has a weight average molecular weight ranging from 40,000 to 80,000.

The polysaccharide hydroxy groups are reacted with an unsaturated group-introducing compound. Suitable unsaturated group-introducing compounds for use in making biodegradable hydrogels include, for example, acryloyl chloride, methacryloyl chloride, acrylic acid, methacrylic acid, or isocyanate having an unsaturated, e.g., vinyl, group at one end of the molecule, e.g., allyl isocyanate or isocyanatoethyl methacrylate.

The percentages of (A) and (B), the molecular weight of the hydrophobic macromer, the molecular weight of the hydrophilic polymer, and the degree of substitution in the hydrophilic polymer, are variables affecting hydrophobicity/hydrophilicity, mechanical, swelling ratio and biodegradation properties of the hydrogel prepared from the hydrogel-forming systems described herein. The "swelling ratio" is obtained by immersing a known weight of dry hydrogel in a vial containing 15 ml liquid, removing swollen hydrogel from the liquid at regular time intervals wiping off surface water and weighing, until equilibrium is obtained.

Decreasing the percentage of (B) and increasing the percentage of (A) increases hydrophobicity (and compatibility with hydrophobic agents and milieus) and decreases swelling ratio (with the largest percentage decrease in swelling ratio being found in decreasing the percentage of (B) from 80% to 60% and increasing the percentage of (A) from 20% to 40%). Increasing the percentage of (B) and decreasing the percentage of (A) increases hydrophilicity and compatibility of hydrogel with hydrophilic agents and milieus. Increasing the percentage of (A) improved mechanical properties in the hydrogels formed from the hydrogel-forming systems. Increasing the molecular weight of (A) increases hydrophobicity and mechanical properties, increases swelling ratio where the percentage of A or B is high and causes increase in biodegradation time for formed hydrogel. Increase in the molecular weight of (B) decreases hydrophobicity, decreases swelling ratio, causes increase in mechanical properties, and where (B) is a dextran derivative increases time for degradation by dextranase, in formed hydrogel. Increase in degree of substitution in hydrophilic polymer decreases hydrophilicity and swelling ratio (in higher weight percentage dextran derivative compositions), increases mechanical property and increases degradation time, in formed hydrogel.

The hydrogel formed herein can chemically incorporate a wound-healing bioactive agent which reacts with either or both of the components of the hydrogel-forming system; this can be accomplished by reacting the bioactive agent with one or both of the components of the hydrogel-forming system herein.

Wound-healing agents which are not reactive with components of the hydrogel-forming system herein can be physically entrapped within the hydrogel or physically encapsulated within the hydrogel by including them in the reaction mixture subjected to photocrosslinking so that the photocrosslinking causes formation of hydrogel with bioactive agent entrapped therein or encapsulated thereby.

By varying the parameters as discussed above, to vary mechanical properties, hydrophobicity/hydrophilicity, swelling ratio and biodegradation properties, the hydrogel-forming system described herein can be tailored to produce hydrogels that control the release rate from the invention wound dressings and device coatings of the precursor cells and/or conditioned medium as well as bioactive agents dispersed therein. As described above, higher swelling ratios give faster release rates and are connected with high hydrophilicity, which is important for wound cleaning utilities, and provide better absorption for sanitary purposes. In one embodiment, the invention wound dressings utilize the hydrogels containing precursor cells as scaffolds for tissue engineering.

The synthetic or natural polymers that can be incorporated into biodegradable hydrogels include, for example, proteins, peptides, polysaccharides, and polymucosaccharides. Proteins for this alternative include, for example, lysozyme, interleukin-1, and basic fibroblast growth factor. This alternative provides a good approach for controlled release administration of synthetic or natural polymer drugs.

Entrapped precursor cells, conditioned medium and wound-healing bioactive agents are readily incorporated into the biodegradable hydrogel by forming a solution of components (A) and (B) to provide a concentration of 30 to 50% (w/v) of total of (A) and (B) in the solution, adding photo initiator and then adding, for example, from 0.5 to 3% (w/w based on the total weight of (A) and (B)) of cells and molecules to be entrapped, and then effecting free radical polymerization. The solvent should be one in which (A) and (B), and agent to be entrapped are soluble. Such solvents in which (A) and (B) are soluble typically include, for example, dimethyl fluoride (DMF) and dimethyl sulfoxide (DMSO), and selection is made from among the solvents in which (A) and (B) are soluble, to obtain solvent that also dissolves the cells and bioactive agent to be entrapped.

Additional Bioactive Agents

As used herein in connection with wound-healing dressings and implants, an "additional bioactive agent" refers to a therapeutic or diagnostic agents other than the "wound-healing" agents described above that promote the natural wound healing process of re-endothelialization of vessels as disclosed herein. Such additional bioactive agents can also be dispersed within a polymer matrix or coating on the surface of insertable or implantable medical or therapeutic devices having different treatment aims as are known in the art, wherein contact of the polymer coating with a treatment surface or blood borne cell or factor or release from the polymer coating by biodegradation is desirable.

Specifically, such additional bioactive agent can include, but are not limited to, one or more: polynucleotides, polypeptides, oligonucleotides, nucleotide analogs, nucleoside analogs, polynucleic acid decoys, therapeutic antibodies, abciximab, blood modifiers, anti-platelet agents, anti-coagulation agents, immune suppressive agents, anti-neoplastic agents, anti-cancer agents, anti-cell proliferation agents, and nitric oxide releasing agents.

The polynucleotide can include deoxyribonucleic acid (DNA), ribonucleic acid (RNA), double stranded DNA, double stranded RNA, duplex DNA/RNA, antisense polynucleotides, functional RNA or a combination thereof. In one embodiment, the polynucleotide can be RNA. In another embodiment, the polynucleotide can be DNA. In another embodiment, the polynucleotide can be an antisense polynucleotide. In another embodiment, the polynucleotide can be a sense polynucleotide. In another embodiment, the polynucleotide can include at least one nucleotide analog. In another embodiment, the polynucleotide can include a phosphodiester linked 3'-5' and 5'-3' polynucleotide backbone. Alternatively, the polynucleotide can include non-phosphodiester linkages, such as phosphotioate type, phosphoramidate and peptide-nucleotide backbones. In another embodiment, moieties can be linked to the backbone sugars of the polynucleotide. Methods of creating such linkages are well known to those of skill in the art.

The polynucleotide can be a single-stranded polynucleotide or a double-stranded polynucleotide. The polynucleotide can have any suitable length. Specifically, the polynucleotide can be about 2 to about 5,000 nucleotides in length, inclusive; about 2 to about 1000 nucleotides in length, inclusive; about 2 to about 100 nucleotides in length, inclusive; or about 2 to about 10 nucleotides in length, inclusive.

An antisense polynucleotide is typically a polynucleotide that is complimentary to an mRNA, which encodes a target protein. For example, the mRNA can encode a cancer promoting protein i.e., the product of an oncogene. The antisense polynucleotide is complimentary to the single-stranded mRNA and will form a duplex and thereby inhibit expression of the target gene, i.e., will inhibit expression of the oncogene. The antisense polynucleotides of the invention can form a duplex with the mRNA encoding a target protein and will disallow expression of the target protein.

A "functional RNA" refers to a ribozyme or other RNA that is not translated.

A "gene therapy agent" refers to an agent that causes expression of a gene product in a target cell through introduction of a gene into the target cell followed by expression of the gene product. An example of such a gene therapy agent would be a genetic construct that causes expression of a protein, such as insulin, when introduced into a cell. Alternatively, a gene therapy agent can decrease expression of a gene in a target cell. An example of such a gene therapy agent would be the introduction of a polynucleic acid segment into a cell that would integrate into a target gene and disrupt expression of the gene. Examples of such agents include viruses and polynucleotides that are able to disrupt a gene through homologous recombination. Methods of introducing and disrupting genes within cells are well known to those of skill in the art.

An oligonucleotide of the invention can have any suitable length. Specifically, the oligonucleotide can be about 2 to about 100 nucleotides in length, inclusive; up to about 20 nucleotides in length, inclusive; or about 15 to about 30 nucleotides in length, inclusive. The oligonucleotide can be single-stranded or double-stranded. In one embodiment, the oligonucleotide can be single-stranded. The oligonucleotide can be DNA or RNA. In one embodiment, the oligonucleotide can be DNA. In one embodiment, the oligonucleotide can be synthesized according to commonly known chemical methods. In another embodiment, the oligonucleotide can be obtained from a commercial supplier. The oligonucleotide can include, but is not limited to, at least one nucleotide analog, such as bromo derivatives, azido derivatives, fluorescent derivatives or a combination thereof. Nucleotide analogs are well known to those of skill in the art. The oligonucleotide can include a chain terminator. The oligonucleotide can also be used, e.g., as a cross-linking reagent or a fluorescent tag. Many common linkages can be employed to couple an oligonucleotide to another moiety, e.g., phosphate, hydroxyl, etc. Additionally, a moiety may be linked to the oligonucleotide through a nucleotide analog incorporated into the oligonucleotide. In another embodiment, the oligonucleotide can include a phosphodiester linked 3'-5' and 5'-3' oligonucleotide backbone. Alternatively, the oligonucleotide can include non-phosphodiester linkages, such as phosphotioate type, phosphoramidate and peptide-nucleotide backbones. In another embodiment, moieties can be linked to the backbone sugars of the oligonucleotide. Methods of creating such linkages are well known to those of skill in the art.

Nucleotide and nucleoside analogues are well known in the art. Examples of such nucleoside analogs include, but are not limited to, Cytovene® (Roche Laboratories), Epivir® (Glaxo Wellcome), Gemzar® (Lilly), Hivid® (Roche Laboratories), Rebetron® (Schering), Videx® (Bristol-Myers Squibb), Zerit® (Bristol-Myers Squibb), and Zovirax® (Glaxo Wellcome). See, *Physician's Desk Reference,* 2004 Edition.

Polypeptides acting as additional bioactive agents dispersed within the polymers in the invention wound dressings and coatings on implantable medical devices can have any suitable length. Specifically, the polypeptides can be about 2 to about 5,000 amino acids in length, inclusive; about 2 to about 2,000 amino acids in length, inclusive; about 2 to about 1,000 amino acids in length, inclusive; or about 2 to about 100 amino acids in length, inclusive.

The polypeptides can also include "peptide mimetics." Peptide analogs are commonly used in the pharmaceutical industry as non-peptide bioactive agents with properties analogous to those of the template peptide. These types of non-peptide compound are termed "peptide mimetics" or "peptidomimetics." Fauchere, J. (1986) *Adv. Bioactive agent Res.,* 15:29; Veber and Freidinger (1985) TINS p. 392; and Evans et al. (1987) *J. Med. Chem.,* 30:1229; and are usually developed with the aid of computerized molecular modeling.

Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH$_2$NH—, —CH$_2$S—, CH$_2$—CH$_2$—, —CH═CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., *Vega Data* (March 1983), 1(3), "Peptide Backbone Modifications" (general review); Morley, J. S., *Trends. Pharm. Sci.,* (1980) pp. 463-468 (general review); Hudson, D. et al., *Int. J. Pept. Prot. Res.,* (1979) 14:177-185 (—CH$_2$NH—, CH$_2$CH$_2$—); Spatola, A. F. et al., *Life Sci.,* (1986) 38:1243-1249 (—CH$_2$—S—); Harm, M. M., *J Chem. Soc. Perkin Trans I* (1982) 307-314 (—CH═CH—, cis and trans); Almquist, R. G. et al., *J. Med. Chem.,* (1980) 23:2533 (—COCH$_2$—); Jennings-Whie, C. et al., *Tetrahedron Lett.,* (1982) 23:2533 (—COCH$_2$—); Szelke, M. et al., European Appln., EP 45665 (1982) CA: 97:39405 (1982) (—CH(OH)CH$_2$—); Holladay, M. W. et al., Tetrahedron Lett., (1983) 24:4401-4404 (—C(OH)CH$_2$—); and Hruby, V. J., *Life Sci.,* (1982) 31:189-199 (—CH$_2$—S—). Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a polypeptide (e.g., with a D-Lysine in place of L-Lysine) may be used to generate more stable polypeptides and polypeptides resistant to endogenous proteases.

In one embodiment, the additional bioactive agent polypeptide dispersed in the polymers or hydrogels used in the invention wound dressings, implants and coatings of medical devices can be an antibody. In one aspect, the antibody can bind to a cell adhesion molecule, such as a cadherin, integrin or selectin. In another aspect, the antibody can bind to an extracellular matrix molecule, such as collagen, elastin, fibronectin or laminin. In still another aspect, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies attached to polymers (either directly or by a linker) can also bind to platelet aggregation factors (e.g., fibrinogen), cell proliferation factors (e.g., growth factors and cytokines), and blood clotting factors (e.g., fibrinogen). In another embodiment, an antibody can be conjugated to an active agent, such as a toxin. In another embodiment, the antibody can be Abciximab (ReoProR)). Abciximab is a Fab fragment of a chimeric antibody that binds to beta(3) integrins. Abciximab is specific for platelet glycoprotein IIb/IIIa receptors, e.g., on blood cells. Human aortic smooth muscle cells express alpha(v)beta (3) integrins on their surface. Treating beta(3) expressing smooth muscle cells may prohibit adhesion of other cells and decrease cellular migration or proliferation. Abciximab also inhibits aggregation of blood platelets.

Useful anti-platelet or anti-coagulation agents that may be used include, e.g., Coumadin® (DuPont), Fragmin® (Pharmacia & Upjohn), Heparin® (Wyeth-Ayerst), Lovenox®, Normiflo®, Orgaran® (Organon), Aggrastat® (Merck), Agrylin® (Roberts), Ecotrin® (Smithkline Beecham), Flolan® (Glaxo Wellcome), Halfprin® (Kramer), Integrillin® (COR Therapeutics), Integrillin® (Key), Persantine® (Boehringer Ingelheim), Plavix® (Bristol-Myers Squibb), ReoPro® (Centecor), Ticlid® (Roche), Abbokinase® (Abbott), Activase® (Genentech), Eminase® (Roberts), and Strepase® (Astra). See, *Physician's Desk Reference,* 2001 Edition. Specifically, the anti-platelet or anti-coagulation agent can include trapidil (avantrin), cilostazol, heparin, hirudin, or ilprost. Trapidil is chemically designated as N,N-dimethyl-5-methyl-[1,2,4]triazolo[1,-5-a]pyrimidin-7-amine. Cilostazol is chemically designated as 6-[4-(1-cyclohexyl-1H-tetrazol-5-yl)-butoxy]-3,4-dihydro-2(1H)-quinolinone. Heparin is a glycosaminoglycan with anticoagulant activity; a heterogeneous mixture of variably sulfonated polysaccharide chains composed of repeating units of D-glucosamine and either L-iduronic or D-glucuronic acids. Hirudin is an anticoagulant protein extracted from leeches, e.g., *Hirudo medicinalis*. Iloprost is chemically designated as 5-[Hexahydro-5-hydroxy-4-(3-hydroxy-4-methyl-1-octen-6-ynyl)-2(1H)-pentalenylidene]pentanoic acid.

The immune suppressive agent can include, e.g., Azathioprine® (Roxane), BayRho-D® (Bayer Biological), CellCept® (Roche Laboratories), Imuran® (Glaxo Wellcome), MiCRhoGAM® (Ortho-Clinical Diagnostics), Neoran® (Novartis), Orthoclone OKT3® (Ortho Biotech), Prograf® (Fujisawa), PhoGAM® (Ortho-Clinical Diagnostics), Sandimmune® (Novartis), Simulect® (Novartis), and Zenapax® (Roche Laboratories).

Specifically, the immune suppressive agent can include rapamycin or thalidomide. Rapamycin is a triene macrolide isolated from *Streptomyces hygroscopicus*. Thalidomide is chemically designated as 2-(2,6-dioxo-3-piperidinyl)-1H-iso-indole-1,3(2H)-dione.

Anti-cancer or anti-cell proliferation agents that can be incorporated as an additional bioactive agent in the invention wound dressings, implants and device coatings include, e.g., nucleotide and nucleoside analogs, such as 2-chloro-deoxyadenosine, adjunct antineoplastic agents, alkylating agents, nitrogen mustards, nitrosoureas, antibiotics, antimetabolites, hormonal agonists/antagonists, androgens, antiandrogens, antiestrogens, estrogen and nitrogen mustard combinations, gonadotropin releasing hormone (GNRH) analogues, progestins, immunomodulators, miscellaneous antineoplastics, photosensitizing agents, and skin and mucous membrane agents. See, *Physician's Desk Reference,* 2005 Edition.

Suitable adjunct antineoplastic agents include Anzemet® (Hoeschst Marion Roussel), Aredia® (Novartis), Didronel® (MGI), Diflucan® (Pfizer), Epogen® (Amgen), Ergamisol® (Janssen), Ethyol® (Alza), Kytril® (SmithKline Beecham), Leucovorin® (Immunex), Leucovorin® (Glaxo Wellcome), Leucovorin® (Astra), Leukine® (Immunex), Marinol® (Roxane), Mesnex® (Bristol-Myers Squibb Oncology/Immunology), Neupogen (Amgen), Procrit® (Ortho Biotech), Salagen® (MGI), Sandostatin® (Novartis), Zinecard® (Pharmacia and Upjohn), Zofran® (Glaxo Wellcome) and Zyloprim® (Glaxo Wellcome).

Suitable miscellaneous alkylating agents include Myleran® (Glaxo Wellcome), Paraplatin® (Bristol-Myers Squibb Oncology/Immunology), Platinol® (Bristol-Myers Squibb Oncology/Immunology) and Thioplex® (Immunex).

Suitable nitrogen mustards include Alkeran® (Glaxo Wellcome), Cytoxan® (Bristol-Myers Squibb Oncology/Immunology), Ifex® (Bristol-Myers Squibb Oncology/Immunology), Leukeran® (Glaxo Wellcome) and Mustargen® (Merck).

Suitable nitrosoureas include BiCNU® (Bristol-Myers Squibb Oncology/Immunology), CeeNU® (Bristol-Myers Squibb Oncology/Immunology), Gliadel® (Rhone-Poulenc Rover) and Zanosar® (Pharmacia and Upjohn).

Suitable antimetabolites include Cytostar-U® (Pharmacia and Upjohn), Fludara® (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

Suitable androgens include Nilandron® (Hoechst Marion Roussel) and Teslac® (Bristol-Myers Squibb Oncology/Immunology).

Suitable antiandrogens include Casodex® (Zeneca) and Eulexin® (Schering).

Suitable antiestrogens include Arimidex® (Zeneca), Fareston® (Schering), Femara® (Novartis) and Nolvadex® (Zeneca).

Suitable estrogen and nitrogen mustard combinations include Emcyt® (Pharmacia and Upjohn).

Suitable estrogens include Estrace® (Bristol-Myers Squibb) and Estrab® (Solvay).

Suitable gonadotropin releasing hormone (GNRH) analogues include Leupron Depot® (TAP) and Zoladex® (Zeneca).

Suitable progestins include Depo-Provera® (Pharmacia and Upjohn) and Megace® (Bristol-Myers Squibb Oncology/Immunology).

Suitable immunomodulators include Erganisol® (Janssen) and Proleukin® (Chiron Corporation).

Suitable miscellaneous antineoplastics include Camptosare (Pharmacia and Upjohn), Celestone® (Schering), DTIC-Dome® (Bayer), Elspar® (Merck), Etopophos® (Bristol-Myers Squibb Oncology/Immunology), Etopoxide® (Astra), Gemzar® (Lilly), Hexalen® (U.S. Bioscience), Hycantin® (SmithKline Beecham), Hydrea® (Bristol-Myers Squibb Oncology/Immunology), Hydroxyurea® (Roxane), Intron A® (Schering), Lysodren® (Bristol-Myers Squibb Oncology/Immunology), Navelbine® (Glaxo Wellcome), Oncaspar® (Rhone-Poulenc Rover), Oncovin® (Lilly), Proleukin® (Chiron Corporation), Rituxan® (IDEC), Rituxan® (Genentech), Roferon-A® (Roche Laboratories), Taxol® (paclitaxol/paclitaxel, Bristol-Myers Squibb Oncology/Immunology), Taxotere® (Rhone-Poulenc Rover), TheraCys® (Pasteur Merieux Connaught), Tice BCG® (Organon), Velban® (Lilly), VePesid® (Bristol-Myers Squibb Oncology/Immunology), Vesanoid® (Roche Laboratories) and Vumon® (Bristol-Myers Squibb Oncology/Immunology).

Suitable photosensitizing agents include Photofrin® (Sanofi).

Specifically, useful anti-cancer or anti-cell proliferation agents can include Taxol® (paclitaxol), a nitric oxide-like compound, or NicOX (NCX-4016). Taxol® (paclitaxol) is chemically designated as 5β,20-Epoxy-1,2α4,7β,10β,13α-hexahydroxytax-11-en-9-one 4,10-diacetate 2-benzoate 13-ester with (2R,3S)-N-benzoyl-3-phenylisoserine, rapamycin, sirolimus, everolimus, paclitaxel and its taxene analogs, 17AAG and other geldanamycins, Epothilone D and other epothilones, Estradiol and related steroid derivatives; Lantrunculin D, Cytochalasin A, nitric oxide, dexamethasone, and Angiopeptin. Anti-proliferant drugs can be used to treat a wide range of abnormal growth related indications resulting from excessive cell proliferation, including, but not limited to restenosis, hemangiomas (vascular malformations); inflammatory conditions, malignant or benign neoplasia, endometriosis, (congenital or endocrine/hormonal abnormalities), adhesions (abdominal or plural), keloid formation, bone overgrowth and infections.

A nitric oxide-like compound includes any compound (e.g., polymer) to which is bound a nitric oxide releasing functional group. Suitable nitric oxide-like compounds are S-nitrosothiol derivative (adduct) of bovine or human serum albumin and as disclosed, e.g., in U.S. Pat. No. 5,650,447. See, e.g., "Inhibition of neointimal proliferation in rabbits after vascular injury by a single treatment with a protein adduct of nitric oxide"; David Marks et al. *J Clin. Invest.* (1995) 96:2630-2638. NCX-4016 is chemically designated as 2-acetoxy-benzoate 2-(nitroxymethyl)-phenyl ester, and is an antithrombotic agent.

It is appreciated that those skilled in the art understand that the bioactive agent useful in the present invention is the bioactive substance present in any of the bioactive agents or agents disclosed above. For example, Taxol® is typically available as an injectable, slightly yellow viscous solution. The bioactive agent, however, is a crystalline powder with the chemical name 5β,20-Epoxy-1,2α4,7β,10β,13α-hexahydroxytax-11-en-9-one 4,10-diacetate 2-benzoate 13-ester with (2R,3S)-N-benzoyl-3-phenylisoserine. *Physician's Desk Reference* (PDR), Medical Economics Company (Montvale, N.J.), (53rd Ed.), pp. 1059-1067.

Preferred bioactive agents and drugs for inclusion in the invention wound dressings and device coatings include, rapamycin and any of its analogs or derivatives, paclitaxel or any of its taxene analogs or derivatives, everolimus, Sirolimus, tacrolimus, or any of its—limus named family of drugs, and statins such as simvastatin, atorvastatin, fluvastatin, pravastatin, lovastatin, rosuvastatin, geldanamycins, such as 17AAG (17-allylamino-17-demethoxygeldanamycin); Kosan KOS-862, 17-dimethylaminoethylamino-17-demethoxy-geldanamycin and other polyketide inhibitors of heat shock protein 90 (Hsp90) and Cilostazol, and the like.

As used herein a "residue of a bioactive agent" or "residue of an additional bioactive agent" is a radical of such bioactive agent as disclosed herein having one or more open valences. Any synthetically feasible atom or atoms of the bioactive agent can be removed to provide the open valence, provided bioactivity is substantially retained when the radical is attached to a residue of compound of structural formulas s (I, III, and V-IX). Based on the linkage that is desired, those skilled in the art can select suitably functionalized starting materials that can be derived from a bioactive agent using procedures that are known in the art.

The residue of a bioactive agent can be formed employing any suitable reagents and reaction conditions. Suitable reagents and reaction conditions are disclosed, e.g., in *Advanced Organic Chemistry*, Part B: Reactions and Synthesis, Second Edition, Carey and Sundberg (1983); *Advanced Organic. Chemistry, Reactions, Mechanisms and Structure*, Second Edition, March (1977); and *Comprehensive Organic Transformations*, Second Edition, Larock (1999).

In certain embodiments, the polymer/bioactive agent linkage can degrade to provide a suitable and effective amount of free bioactive agent. As will be appreciated by those of skill in the art, depending upon the chemical and therapeutic properties of the biological agent, in certain other embodiments, the bioactive agent attached to the polymer performs its therapeutic effect while still attached to the polymer, such as is the case with the "sticky" polypeptides Protein A and Protein G, known herein as "ligands", which function while attached to the polymer to hold a target molecule close to the polymer, and the bradykinins and antibodies, which function by contacting (e.g., bumping into) a receptor on a target molecule. Any suitable and effective amount of bioactive agent can be released and will typically depend, e.g., on the specific polymer, bioactive agent, and polymer/bioactive agent linkage chosen. Typically, up to about 100% of the bioactive agent can be released from the polymer by degradation of the polymer/bioactive agent linkage. Specifically, up to about 90%, up to 75%, up to 50%, or up to 25% of the bioactive agent can be released from the polymer. Factors that typically affect the amount of the bioactive agent that is released from the polymer is the type of polymer/bioactive agent linkage, and the nature and amount of additional substances present in the formulation.

The polymer/bioactive agent linkage can be selected to degrade over a desired period of time to provide time release of a suitable and effective amount of bioactive agent according to the type of wound being treated. Any suitable and effective period of time can be chosen by judicious choice of the chemical properties of the linkage of the bioactive agent to the polymer. Typically, the suitable and effective amount of bioactive agent can be released over a time selected from about twenty-four hours, about seven days, about thirty days, about ninety days, and about one hundred and twenty days. Longer time spans are particularly suitable for implantable wound dressings and device coatings. Additional factors that typically affect the length of time over which the bioactive agent is released from the polymer include, e.g., the nature and amount of polymer, the nature and amount of bioactive agent, and the nature and amount of additional substances present in the formulation.

Polymer/Linker/Bioactive Agent Linkage

In addition to being directly linked (e.g., covalently) to the residue of a compound of structural formulas (I, III, and V-IX), the residue of a bioactive agent can also be linked to the residue of a compound of structural formulas (I, III, and V-IX) by a suitable linker. The structure of the linker is not crucial, provided the resulting compound of the invention has an effective therapeutic index as a bioactive agent.

Suitable linkers include linkers that separate the residue of a compound of structural formulas (I, III, and V-IX) from the residue of a bioactive agent by a distance of about 5 angstroms to about 200 angstroms, inclusive. Other suitable linkers include linkers that separate the residue of a compound of structural formulas s (I, III, and V-IX) and the residue of a bioactive agent by a distance of about 5 angstroms to about 100 angstroms, inclusive, as well as linkers that separate the residue of a compound of structural formulas (I, III, and V-IX) from the residue of a bioactive agent by a distance of about 5 angstroms to about 50 angstroms, or by about 5 angstroms to about 25 angstroms, inclusive.

The linker can be linked to any synthetically feasible position on the residue of a compound of structural formulas (I, III, and V-IX). Based on the linkage that is desired, those skilled in the art can select suitably functionalized starting materials that can be derived from a compound of structural formulas (I, III, and V-IX) and a bioactive agent using procedures that are known in the art.

The linker can conveniently be linked to the residue of a compound of structural formulas (I, III, and V-IX) or to the residue of a bioactive agent through an amide (e.g. —N(R)C(=O)— or —C(=O)N(R)—), ester (e.g., —OC(=O)— or —C(=O)O—), ether (e.g., —O—), ketone (e.g., —C(=O)—) thioether (e.g., —S—), sulfinyl (e.g., —S(O)—), sulfonyl (e.g., —S(O)$_2$—), disulfide (e.g., —S—S—), amino (e.g., —N(R)—) or a direct (e.g., C—C) linkage, wherein each R is independently H or (C$_1$-C$_6$)alkyl. The linkage can be formed from suitably functionalized starting materials using synthetic procedures that are known in the art. Based on the linkage that is desired, those skilled in the art can select suitably functionalized starting materials that can be derived from a residue of a compound of structural formulas (I, III, and V-IX), a residue of a bioactive agent, and from a given linker using procedures that are known in the art.

Specifically, the linker can be a divalent radical of the formula W-A-Q wherein A is $(C_1-C_{24})$alkyl, $(C_2-C_{24})$alkenyl, $(C_2-C_{24})$alkynyl, $(C_3-C_8)$cycloalkyl, or $(C_6-C_{10})$ary wherein W and Q are each independently —N(R)C(=O)—, —C(=O)N(R)—, OC(=O)—, —C(=O)O—, —O—, —S—, —S(O)—, —S(O)$_2$—, —S—S—, —N(R)—, —C(=O)—, or a direct bond (i.e., W and/or Q is absent); wherein each R is independently H or $(C_1-C_6)$alkyl.

Specifically, the linker can be a divalent radical of the formula W—(CH$_2$)n-Q, wherein n is from about 1 to about 20, from about 1 to about 15, from about 2 to about 10, from about 2 to about 6, or from about 4 to about 6; wherein W and Q are each independently —N(R)C(=O)—, —C(=O)N(R)—, —OC(=O)—, —C(=O)O—, —O—, —S—, —S(O)—, —S(O)$_2$—, —S—S—, —C(=O)—, —N(R)—, or a direct bond (i.e., W and/or Q is absent); wherein each R is independently H or $(C_1-C_6)$alkyl.

Specifically, W and Q can each independently be —N(R)C(=O)—, —C(=O)N(R)—, —OC(=O)—, —N(R)—, —C(=O)O—, —O—, or a direct bond (i.e., W and/or Q is absent). Specifically, the linker can be a divalent radical formed from a saccharide. Specifically, the linker can be a divalent radical formed from a cyclodextrin. Specifically, the linker can be a divalent radical, i.e., divalent radicals formed from a peptide or an amino acid. The peptide can comprise 2 to about 25 amino acids, 2 to about 15 amino acids, or 2 to about 12 amino acids.

Specifically, the peptide can be poly-L-lysine (i.e., [—NHCH[(CH$_2$)$_4$NH$_2$]CO—]$_m$-Q wherein Q is H, $(C_1-C_{14})$ alkyl, or a suitable carboxy protecting group; and wherein m is about 2 to about 25. The poly-L-lysine can contain about 5 to about 15 residues (i.e., m is from about 5 to about 15). For example, the poly-L-lysine can contain from about 8 to about 11 residues (i.e., m is from about 8 to about 11).

Specifically, the peptide can also be poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, or poly-L-lysine-L-tyrosine.

Specifically, the linker can be prepared from 1,6-diaminohexane H$_2$N(CH$_2$)$_6$NH$_2$, 1,5-diaminopentane H$_2$N(CH$_2$)$_5$NH$_2$, 1,4-diaminobutane H$_2$N(CH$_2$)$_4$NH$_2$, or 1,3-diaminopropane H$_2$N(CH$_2$)$_3$NH$_2$.

One or more bioactive agents can be linked to the polymer through a linker. Specifically, the residue of each of the bioactive agents can each be linked to the residue of the polymer through a linker. Any suitable number of bioactive agents (i.e., residues thereof) can be linked to the polymer (i.e., residue thereof) through a linker. The number of bioactive agents that can be linked to the polymer through a linker can typically depend upon the molecular weight of the polymer and whether the polymer is saturated or unsaturated. For example, up to about 450 bioactive agents (i.e., residues thereof) can be linked to the polymer (i.e., residue thereof) through a linker, up to about 300 bioactive agents (i.e., residues thereof) can be linked to the polymer (i.e., residue thereof) through a linker, or up to about 150 bioactive agents (i.e., residues thereof) can be linked to the polymer (i.e., residue thereof) through a linker.

In one embodiment of the present invention, a polymer (i.e., residue thereof) as disclosed herein can be linked to the linker via a carboxyl group (e.g., COOR$^2$) of the polymer. For example, a polymer residue containing a free hydrogen, or $(C_6-C_{10})$aryl$(C_1-C_6)$alkyl, can react with an amino functional group of the linker or a hydroxyl functional group of the linker, to provide a Polymer/Linker having an amide linkage or a Polymer/Linker having a carboxyl ester linkage, respectively. In another embodiment, the carboxyl group can be transformed into an acyl halide or an acyl anhydride.

In one embodiment of the invention, a bioactive agent (i.e., residue thereof) can be linked to the linker via a carboxyl group (e.g., COOR, wherein R is hydrogen, $(C_6-C_{10})$aryl$(C_1-C_6)$alkyl or $(C_1-C_6)$alkyl) of the linker. Specifically, an amino functional group of the bioactive agent or a hydroxyl functional group of the bioactive agent can react with the carboxyl group of the linker, to provide a Linker/Bioactive agent having an amide linkage or a Linker/Bioactive agent having a carboxylic ester linkage, respectively. In another embodiment, the carboxyl group of the linker can be transformed into an acyl halide or an acyl anhydride.

The bioactive agent is released as the polymer degrades, whether the bioactive agent is linked to the polymer, dissolved within the polymer, or intermixed with the polymer. Any suitable and effective amount of bioactive agent can be released and will typically depend, e.g., on the specific polymer, bioactive agent, linker, and polymer/linker/bioactive agent linkage chosen. Typically, up to about 100% of the bioactive agent can be released from the polymer. Specifically, up to about 90%, up 75%, up to 50%, or up to 25% of the bioactive agent can be released from the polymer. Factors that typically affect the amount of the bioactive agent released from the polymer/linker/bioactive agent include, e.g., the nature and amount of polymer, the nature and amount of bioactive agent, the nature and amount of linker, the nature of any polymer/linker/bioactive agent linkage, and the nature and amount of additional substances present in the formulation.

The polymer degrades over a period of time to provide the suitable and effective amount of bioactive agent. Any suitable and effective period of time can be chosen. Typically, the suitable and effective amount of bioactive agent can be released in about twenty-four hours, in about seven days, in about thirty days, in about ninety days, or in about one hundred and twenty days. Factors that typically affect the length of time in which the precursor cells and/or bioactive agent is released from the polymer include, e.g., the nature and amount of polymer, the nature and amount of precursor cells, conditioned medium or growth medium for the cells, the nature and amount of bioactive agent, the nature of any linker used, the nature of the polymer/linker/bioactive agent linkage, and the nature and amount of additional substances present in the formulation.

Polymer Intermixed with Bioactive Agent or Additional Bioactive Agent

In addition to being linked to one or more bioactive agents, either directly or through a linker, a polymer used for coating a medical device structure as described herein can be physically intermixed with one or more bioactive agents or additional bioactive agents to provide a formulation.

As used herein, "intermixed" refers to a polymer of the present invention physically mixed with a bioactive agent or a polymer as described herein that is physically in contact with a bioactive agent.

As used herein, a "formulation" refers to a polymer as described herein that is intermixed with one or more bioactive agents or additional bioactive agents. The formulation includes such a polymer having one or more bioactive agents present on the surface of the polymer, partially embedded in the polymer, or completely embedded in the polymer. Additionally, the formulation includes a polymer as described herein and a bioactive agent forming a homogeneous composition (i.e., a homogeneous formulation).

Any suitable amount of polymer and bioactive agent can be employed to provide the formulation. The polymer can be present in about 0.1 wt. % to about 99.9 wt. % of the formulation. Typically, the polymer can be present above about 25 wt. % of the formulation; above about 50 wt. % of the formulation; above about 75 wt. % % of the formulation; or above about 90 wt. % of the formulation. Likewise, the bioactive agent can be present in about 0.1 wt. % to about 99.9 wt. % of the formulation. Typically, the bioactive agent can be present above about 5 wt. % of the formulation; above about 10 wt. % of the formulation; above about 15 wt. % of the formulation; or above about 20 wt. % of the formulation.

In yet another embodiment of the invention the polymer/bioactive agent, polymer/linker/bioactive agent, formulation, or combination thereof as described herein, can be applied, as a polymeric film onto the surface of a medical device. At least a portion of the surface of the medical device can be coated with a film of polymer or hydrogel having any suitable thickness. For example, the thickness of the film on the medical device can be about 1 to about 50 microns thick or about 5 to about 20 microns thick.

The polymer and/or hydrogel film can effectively serve to sequester precursor cells or conditioned medium thereof as well as a bioactive agent-eluting coating on a medical device, such as an orthopedic implant. This bioactive coating can be created on the medical device by any suitable coating process, e.g., dip coating, vacuum depositing, or spray coating the polymeric film, on the medical device to create a type of local bioactive agent delivery system that enhances restoration of a tissue lesion at the site of implant.

In one embodiment, the wound dressing is a single or multilayered wound dressing wherein the above-described polymer is in the form of a membrane or mat of fine polymer threads, for example Nanoskin™ (MediVas, LLP, San Diego, Calif.). Such a polymer dressing can be used as a surgical wrap, for example, for restoration of tissue for burn victims when seeded with epithelial precursor cells or infused with conditioned medium obtained from allogenic epithelial precursor cells, wherein a surface barrier enhances tissue restoration and yet the polymer membrane is bioabsorbed. In other embodiments, the polymer threads can be woven, webbed, braided, and the like. For example, electrospinning of the polymer can produce a random webbing or mat of microfibers of the polymer.

At least one surface of the polymer membrane may be coated with an additional formulation layer in a sandwich type of configuration to deliver to the tissue, bioactive agents that promote natural tissue restoration processes. Such an additional layer of hydrogel-based drug release formulation can comprise various bioactive agents dispersed in a hydrogel to provide an elution rate different than that of the polymer component of the wound dressing. Optionally the multilayered wound dressing may further include an occlusive layer lying atop the hydrogel layer.

Any suitable size of polymer and bioactive agent can be employed to provide such a formulation. For example, the polymer can have a size of less than about $1 \times 10^{-4}$ meters, less than about $1 \times 10^{-5}$ meters, less than about $1 \times 10^{-6}$ meters, less than about $1 \times 10^{-7}$ meters, less than about $1 \times 10^{-8}$ meters, or less than about $1 \times 10^{-9}$ meters.

The formulation can degrade to provide a suitable and effective amount of the at least one progenitor precursor cell, which can be autologous or allogenic. Any suitable and effective amount of the precursor cells can be released and will typically depend, e.g., on the specific formulation chosen.

Typically, up to about 100% of the precursor cells or conditioned medium can be released from the formulation. Specifically, up to about 90%, up to 75%, up to 50%, or up to 25% of the precursor cells or conditioned medium can be released from the formulation at a substantially linear rate. Factors that typically affect the amount or rate of the precursor cells or conditioned medium that is released from the formulation include, e.g., the type of tissue in contact with the wound dressing, the nature and amount of polymer or hydrogel, the type of dispersal of the precursor cells in the polymer or hydrogel, the nature and amount of the precursor cells, and the nature and amount of any additional wound healing bioactive agent(s) present in the formulation.

The formulation can degrade over a period of time to provide the suitable and effective amount of bioactive agent. Any suitable and effective period of time can be chosen. For example, the polymer can be selected to release the bioactive agent over about twenty-four hours, over about two days, over about seven days, over about ninety days, or over about one hundred and twenty days, the latter being particularly useful when an implantable wound dressing is desired. Factors that typically affect the length of time over which the bioactive agent is released from the formulation include, e.g., the nature and amount of polymer, the nature and amount of bioactive agent, and the nature and amount of additional substances present in the formulation.

In one embodiment, a polymer used in making an invention wound dressing is physically intermixed with at least one bioactive agent. In another embodiment, the polymer is linked to at least one bioactive agent, either directly or through a linker. In another embodiment, the precursor cells disbursed in the polymer are held within the polymer during polymer biodegradation, either directly or through a ligand or linker, and the polymer or hydrogel can also be physically intermixed with one or more precursor cells in growth medium or with conditioned medium, such as cell-free conditioned medium.

The invention polymer/hydrogel coatings for medical devices containing precursor cells and/or conditioned medium, whether or not present in a formulation as described herein, whether or not linked to a bioactive agent as described herein, and whether or not intermixed with a bioactive agent as described herein, can be used in the manufacture of a medical device. Suitable medical devices include, e.g., artificial joints, artificial bones and intravertebral implants, cardiovascular medical devices, stents, shunts, sutures, artificial arteries, teeth and other body implants.

In yet another embodiment, the invention provides methods for the invention provides methods for promoting restoration of tissue at a lesion site in a mammalian subject by using a biodegradable wound dressing comprising at least one precursor cell selected from stem cells, tissue-specific progenitor cells, germ-layer lineage stem cells, and pluripotent stem cells, and/or conditioned medium obtained from such cells, dispersed within a biodegradable polymer or hydrogel and contacting the lesion site with the wound dressing under conditions suitable for promoting restoration of the tissue at the lesion site.

To this end, in treating a chronic wound, the polymer of the wound dressing can be placed in contact with the wound bed and the precursor cells and conditioned medium can be allowed to interact with cells and factors in surrounding tissue while the polymer biodegrades over a suitable period time, releasing bioactive agents therein into the wound bed while the polymer is absorbed therein. Alternatively, the wound dressing used in treatment of a chronic wound will include a biodegradable hydrogel layer (i.e., non-stick layer), which can be placed in contact with the wound bed. The formulations of the polymer layer and the hydrogel layer can be selected to release their respective cells, conditioned medium and bioactive agents at different rates. The invention methods are beneficially used in treatment of such chronic wounds as venous stasis ulcer, diabetic ulcer, pressure ulcer, or ischemic ulcer.

The following examples are meant to illustrate and not to limit the invention.

EXAMPLES

Example 1

Delivery of Growth/Survival Components by Alginic Acid

This example illustrates experiments that were conducted to test the ability of hydrogel particles to deliver components required for cell growth and survival. The hydrogel particles were formed using low viscosity alginic acid (AA) (Sigma Chemicals, A2158) prepared using an adaptation of a published protocol (J Raymond et al., *Am J Neuroradiol* (2003) 24:1214-1221).

Preliminary experiments demonstrated that 4% low viscosity alginate made up in 0.5% sodium chloride can absorb about one third of its volume of the desired media, such as conditioned medium from progenitor cell cultures that had been isolated from human blood, and then be crosslinked by adding 5% calcium chloride. Polymerization occurs very rapidly and AA particles form, encapsulating the media within the alginate. The rate of release of media from the particles during the first 24 hours is very rapid, with about half of the media being released. The release rate then slows over the next 48 hours until the majority of the media is released by 72 hours.

To illustrate the release rate from AA particles, trypan blue was incorporated into the AA as an indicator compound. The trypan blue-containing beads were placed into wells without PBS, as controls to demonstrate the starting color of the beads, and into wells plus PBS to observe the release of the trypan blue into the colorless PBS. At each time point (24, 48 and 72 hours), the trypan-blue containing beads were removed from the PBS and placed into an empty well to observe any change in color when compared to control beads. Observations were recorded and photographed at each time point.

At 24 hours, about 50% of the blue color had been released from the hydrogel particles, by 48 hours there was still a small amount of color left in the particles, but by 72 hours the AA particles no longer had any color left, indicating that all the trypan blue had been released.

Cell Rescue Experiment

This example illustrates the efficiency of AA particles for delivering a survival component to cells. An experiment was designed using fetal bovine serum (FBS) encapsulated in AA particles, which were provided to cells growing without other access to FBS. Endothelial or smooth muscle cells were plated into 12-well tissue culture plates with FBS-containing particles placed in adjoining cell inserts in the plates (BD 35-3180, pore size 0.4 microns).

The experimental protocol included the following conditions for both endothelial cells and smooth muscle cells:

1. Cells were plated at 15,000 cells/well in 12-well plates in the following media (the basal medium for SMC is SmGM-2 BulletKit (Cambrex, #CC-3182) and for EC is EGM-2 BulletKit (Cambrex #CC-3162)).

2. Complete growth factors (for SMC this included hEGF, insulin, hFGF-B; and for EC this included hEGF, VEGF, hFGF-B, R3-IGF-1) and 5% FBS.

3. Minus growth factors, plus 5% FBS.

4. Minus growth factors, minus serum.

5. Minus growth factors, plus AA particle containing 0% FBS.

6. Minus growth factors, plus AA particle containing 5% FBS.

7. Minus growth factors, plus AA particle containing 10% FBS

AA particles were made as follows: Sterile 4% low viscosity alginic acid (AA) was added to ⅓ (v/v) FBS and then crosslinked by addition of 5% calcium chloride in a volume equal to AA. Particles were rinsed twice in PBS and then placed into cell inserts.

Microscopic observations were made at 24 and 48 hours, and standard ATP assays were conducted at 48 hours to measure cell growth. This same experiment was repeated several times, demonstrating that the AA particles were able to deliver FBS to both endothelial and smooth muscle cells to enhance cell growth (FIG. 1).

Example 2

Encapsulation of Cells in Hydrogel

A highly purified and well-characterized sodium alginate with very low levels of endotoxins and proteins, optimal for in vitro and in vivo applications, was used to encapsulate cells (NovaMatrix, Pronova UltraPure (UP) LVM alginate). This alginate is made up in 2% HEPES with some sonication, to help the AA go into complete suspension, and then filter sterilized. Cell-containing-particles are made by mixing cells plus fetal bovine serum (FBS) with the alginate, drawing the mixture up into a 1 cc syringe and forming particles drop wise into a 5% calcium chloride solution. This process produces about 100 particles/ml with about 2000 cells/particle. The cells used for this experiment were SMCs, which are a robust, anchorage-dependent cell line normally not grown in suspension.

To determine cell viability within the AA particles, two viability dyes were used: (1) Calcein AM, which is retained in cells that have intact membranes. Calcein AM does not label dead cells and is rapidly lost under conditions that cause cell lysis. Once inside the cell, the colorless, nonfluorescent AM ester is cleaved by nonspecific esterases causing the compound to fluoresce. (2) Propidium oodide, which binds to DNA by intercalating between the bases. Propidium Iodide is membrane impermeant and does not easily enter viable cells. Control particles encapsulated SMCs in the AA particles, but were exposed to no dyes. Microscopic observations were recorded and photographed (20× mag Ba=50 microns) using a Nikon Eclipse TE2000-S phase contrast microscope equipped with an epi-fluorescence attachment After up to 6 h the cells were photographed in color. Microscopic observations were recorded and photographed using a Nikon Eclipse TE2000-S phase contrast microscope equipped with an epi-fluorescence attachment and the photographs showed that the Calcein AM was taken up by viable cells while the Propidium Iodide (PI) was not. This result indicated that the cells in the particles were still alive following several hours inside the AA particles.

A series of time course experiments using SMC encapsulated in AA particles exposed to the two viability dyes, indicated that SMCs remained viable for up to 6 hours because the Calcein AM was taken up by encapsulated cells while the propidium iodide was not.

Example 3

Polymer Coating of Hydrogel Encapsulated Cells

PEA conjugated to fluorescent dansyl-lysine was used to coat particles to visualize the polymer coating for consistency and completeness of coating. The results of this experiment indicated that a reliable method to coat AA particles to achieve consistency and completeness of coating was to suspend them in the polymer and allow the polymer to flow through a mesh that captures the particles. The particles were then rapidly removed from the mesh by resuspending in the appropriate buffer.

Then, to determine if the SMCs contained in AA particles can survive coating with PEA.H polymer, AA particles were formed containing 2000 smooth muscle cells/particle. Test AA particles were coated with a 10% (w/v ethanol) polymer solution and incubated in the presence of the two viability dyes shown in Example 2 above as able to enter the encapsulated cells. Control particles encapsulated the SMCs, but were also exposed to the dyes, but were not coated with the PEA polymer. Microscopic observations were recorded and photographed (200× mag; Bar=50 microns) using a Nikon Eclipse TE2000-S phase contrast microscope equipped with an epi-fluorescence attachment.

It had been demonstrated in Example 2 above, that SMCs in AA particles remained viable for up to 6 hours as measured by Calcein AM uptake and propidium iodide exclusion. Visual examination of these polymer-coated particles after 4 four hours indicated that the overall cell population was less viable than the cells in the control particles. Cells nearest the surface were most affected by the polymer coating; whereas some of the more interior cells were able to survive for a few hours. Therefore, polymer coating of the AA-encapsulated SMCs reduced the length of time that the cells were viable, but the principle of polymer encapsulation of cells was demonstrated.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

Although the invention has been described with reference to the above examples, it will be understood that modifications and variations are encompassed within the spirit and scope of the invention. Accordingly, the invention herein is limited only by the following claims.

What is claimed is:

1. A bioactive wound dressing comprising:
a biodegradable poly(ester amide) (PEA) polymer having a formula (I):

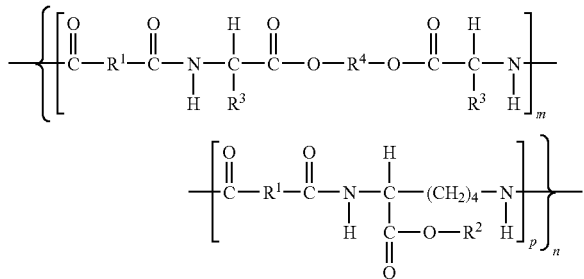

wherein
n ranges from about 5 to about 150;
m ranges from about 0.1 to about 0.9;
p ranges from about 0.9 to about 0.1;
$R^1$ is ($C_2$-$C_{20}$) alkyl;
$R^2$ is hydrogen;
$R^3$ is ($C_1$-$C_6$) alkyl; and
$R^4$ is ($C_2$-$C_{20}$) alkyl;
at least one precursor cell selected from the group consisting of stem cells, mesenchymal stem cells, tissue-specific progenitor cells, germ-layer stem cells, and pluripotent stem cells, and combinations thereof; and
at least one bioactive agent;
the at least one precursor cell and the at least one bioactive agent being dispersed within the biodegradable polymer, and the at least one bioactive agent being attached to the polymer by a covalent bond.

2. The wound dressing of claim 1, wherein the wound dressing is implantable.

3. The wound dressing of claim 1, wherein the polymer further comprises a suitable growth medium for the cells.

4. The wound dressing of claim 1, wherein the at least one precursor cell promotes in situ tissue repair and remodeling in epithelial, mesenchymal, neural or visceral organ tissue.

5. The wound dressing of claim 4, wherein the at least one precursor cell is selected from the group consisting of a limbal stem cell, a dental epithelial stem cell, and a progenitor cell of human breast epithelium.

6. The wound dressing of claim 1, wherein the at least one precursor cell is a mesenchymal stem cell or progenitor cell obtained from bone marrow.

7. The wound dressing of claim 1, wherein the at least one precursor cell is a renal stem cell or a renal progenitor cell.

8. The wound dressing of claim 1, wherein the at least one precursor cell is a neural stem cell or a neural precursor cell.

9. The wound dressing of claim 1, further comprising at least one additional bioactive agent dispersed within the polymer.

10. The wound dressing of claim 1, wherein $R^4$ is selected from the group consisting of —($CH_2$)$_4$—, and —($CH_2$)$_6$—.

11. The wound dressing of claim 1, wherein the polymer produces at least one α-amino acid upon biodegradation.

12. The wound dressing of claim 1, wherein the at least one bioactive agent is released from the wound dressing under physiological conditions.

13. The wound dressing of claim 1, wherein the at least one precursor cell dispersed in the polymer is released in situ as a result of biodegradation of the polymer.

14. The wound dressing of claim 1, further comprising a hydrogel layer, wherein the polymer and the hydrogel are in separate, but contiguous layers.

15. The wound dressing of claim 14, further comprising an occlusive layer covering the hydrogel layer.

16. The wound dressing of claim 14, wherein the hydrogel has hydrophobic and hydrophilic components and a one-phase crosslinked polymer network structure.

17. The wound dressing of claim 16, wherein the wound dressing further comprises a suitable growth medium in the hydrogel.

18. The wound dressing of claim 1, further comprising at least one wound-healing agent selected from the group consisting of ligands, extracellular matrix proteins, proteinaceous growth factors, antimicrobials, anti-inflammatory agents, healing promoters, biocompatible glycoproteins or combinations thereof.

19. The wound dressing of claim 1, wherein the polymer is in the form of a woven or webbed material.

20. The wound dressing of claim 1, wherein the polymer biodegrades to release the precursor cells over a period ranging from about twenty-four hours to about one hundred and twenty days.

21. A method for promoting restoration of tissue at a lesion site in a mammalian subject, said method comprising:
   contacting the lesion site with the wound dressing of claim 1 under conditions suitable for promoting restoration of the tissue at the lesion site.

22. The method of claim 21, wherein the polymer biodegrades over a period ranging from about twenty-four to about one hundred and twenty days.

23. The method of claim 21, wherein the wound dressing is surgically implanted in the subject at the lesion site.

24. The method of claim 21, wherein the subject is a human, pet or farm animal, or racehorse.

25. The method of claim 21, wherein the precursor cells are autologous to the subject.

26. The method of claim 25, wherein the polymer further comprises a suitable growth medium for the cells.

27. The method of claim 21, wherein the at least one precursor cell is allogeneic to the subject.

28. The method of claim 27, wherein the at least one precursor cell promotes in situ tissue repair and remodeling in epithelial, mesenchymal, neural or visceral organ tissue.

29. The method of claim 27, wherein the at least one precursor cell is selected from the group consisting of a limbal stem cell, a dental epithelial stem cell and a progenitor cell of human breast epithelium.

30. The method of claim 27, wherein the precursor cell is selected from a mesenchymal stem cell or progenitor cell obtained from bone marrow.

31. The method of claim 27, wherein the at least one precursor cell is a renal stem cell or a renal progenitor cell.

32. The method of claim 27, wherein the at least one precursor cell is a neural stem cell or a neural precursor cell.

\* \* \* \* \*

SEQUENCE LISTING

```
<160> NUMBER OF SEQ ID NOS: 8

<210> SEQ ID NO 1
<211> LENGTH: 61
<212> TYPE: PRT
<213> ORGANISM: Artificial sequence
<220> FEATURE:
<223> OTHER INFORMATION: Synthetic construct

<400> SEQUENCE: 1

Met Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Gly Val Asp Gly Val Trp
        35                  40                  45

Thr Tyr Asp Asp Ala Thr Lys Thr Phe Thr Val Thr Glu
    50                  55                  60

<210> SEQ ID NO 2
<211> LENGTH: 55
<212> TYPE: PRT
<213> ORGANISM: Artificial sequence
<220> FEATURE:
<223> OTHER INFORMATION: Synthetic construct

<400> SEQUENCE: 2

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45
```

```
Lys Thr Phe Thr Val Thr Glu
    50              55

<210> SEQ ID NO 3
<211> LENGTH: 61
<212> TYPE: PRT
<213> ORGANISM: Artificial sequence
<220> FEATURE:
<223> OTHER INFORMATION: Synthetic construct

<400> SEQUENCE: 3

Met Thr Pro Ala Val Thr Thr Tyr Lys Leu Val Ile Asn Gly Lys Thr
1               5                   10                  15

Leu Lys Gly Glu Thr Thr Thr Lys Ala Val Asp Ala Glu Thr Ala Glu
            20                  25                  30

Lys Ala Phe Lys Gln Tyr Ala Asn Asp Asn Gly Val Asp Gly Val Trp
        35                  40                  45

Thr Tyr Asp Asp Ala Thr Lys Thr Phe Thr Val Thr Glu
    50                  55                  60

<210> SEQ ID NO 4
<211> LENGTH: 55
<212> TYPE: PRT
<213> ORGANISM: Artificial sequence
<220> FEATURE:
<223> OTHER INFORMATION: Synthetic construct

<400> SEQUENCE: 4

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50              55

<210> SEQ ID NO 5
<211> LENGTH: 10
<212> TYPE: PRT
<213> ORGANISM: Artificial sequence
<220> FEATURE:
<223> OTHER INFORMATION: Synthetic construct

<400> SEQUENCE: 5

Lys Arg Pro Pro Gly Phe Ser Pro Phe Arg
1               5                   10

<210> SEQ ID NO 6
<211> LENGTH: 9
<212> TYPE: PRT
<213> ORGANISM: Artificial sequence
<220> FEATURE:
<223> OTHER INFORMATION: Synthetic construct

<400> SEQUENCE: 6

Lys Arg Pro Pro Gly Phe Ser Pro Phe
1               5

<210> SEQ ID NO 7
<211> LENGTH: 9
<212> TYPE: PRT
<213> ORGANISM: Artificial sequence
<220> FEATURE:
```

```
-continued

<223> OTHER INFORMATION: Synthetic construct

<400> SEQUENCE: 7

Arg Pro Pro Gly Phe Ser Pro Phe Arg
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic construct

<400> SEQUENCE: 8

Arg Pro Pro Gly Phe Ser Pro Phe
1               5
```